(12) United States Patent
Chateau et al.

(10) Patent No.: US 10,723,848 B2
(45) Date of Patent: Jul. 28, 2020

(54) MASTERBATCH COMPOSITION COMPRISING A HIGH CONCENTRATION OF BIOLOGICAL ENTITIES

(71) Applicant: CARBIOS, Saint-Beauzire (FR)

(72) Inventors: Michel Chateau, Riom (FR); Jean-Philippe Rousselle, Beaumont-le-Roger (FR)

(73) Assignee: CARBIOS, Saint-Beauzire (FR)

( * ) Notice: Subject to any disclaimer, the term of this patent is extended or adjusted under 35 U.S.C. 154(b) by 94 days.

(21) Appl. No.: 15/580,702

(22) PCT Filed: Jun. 10, 2016

(86) PCT No.: PCT/EP2016/063369
§ 371 (c)(1),
(2) Date: Dec. 8, 2017

(87) PCT Pub. No.: WO2016/198650
PCT Pub. Date: Dec. 15, 2016

(65) Prior Publication Data
US 2018/0186943 A1 Jul. 5, 2018

(30) Foreign Application Priority Data

Jun. 12, 2015 (EP) .................................... 15305903

(51) Int. Cl.
| | | |
|---|---|---|
| *C08L 3/02* | (2006.01) | |
| *C08J 3/22* | (2006.01) | |
| *B29C 48/40* | (2019.01) | |
| *C08L 101/16* | (2006.01) | |
| *C08J 3/20* | (2006.01) | |
| *C08L 67/02* | (2006.01) | |
| *C08L 89/00* | (2006.01) | |
| *C08L 67/04* | (2006.01) | |
| *C08J 5/00* | (2006.01) | |
| *C08J 5/18* | (2006.01) | |
| *C12N 9/20* | (2006.01) | |
| *C12N 9/50* | (2006.01) | |
| *C12N 9/52* | (2006.01) | |
| *C08K 3/26* | (2006.01) | |
| *C08K 3/34* | (2006.01) | |
| *C08K 5/00* | (2006.01) | |
| *C08K 7/14* | (2006.01) | |
| *C08L 99/00* | (2006.01) | |
| *C08K 3/22* | (2006.01) | |

(52) U.S. Cl.
CPC ............. *C08J 3/226* (2013.01); *B29C 48/402* (2019.02); *C08J 3/20* (2013.01); *C08J 3/203* (2013.01); *C08J 5/00* (2013.01); *C08J 5/18* (2013.01); *C08K 3/26* (2013.01); *C08K 3/34* (2013.01); *C08K 5/0033* (2013.01); *C08K 7/14* (2013.01); *C08L 3/02* (2013.01); *C08L 67/02* (2013.01); *C08L 67/04* (2013.01); *C08L 89/00* (2013.01); *C08L 99/00* (2013.01); *C08L 101/16* (2013.01); *C12N 9/20* (2013.01); *C12N 9/50* (2013.01); *C12N 9/52* (2013.01); *C12Y 304/21062* (2013.01); *C08J 2300/16* (2013.01); *C08J 2301/02* (2013.01); *C08J 2303/04* (2013.01); *C08J 2323/02* (2013.01); *C08J 2333/24* (2013.01); *C08J 2367/00* (2013.01); *C08J 2367/04* (2013.01); *C08J 2489/00* (2013.01); *C08K 2003/2206* (2013.01); *C08K 2003/265* (2013.01); *C08K 2201/018* (2013.01); *C08L 2201/06* (2013.01)

(58) Field of Classification Search
CPC ..... C08J 3/226; C08J 3/20; C08J 3/203; C08J 5/00; C08J 5/18; C08K 3/26; C08K 3/34; C08K 7/14; C08L 3/02; C08L 67/02; C08L 67/04; C08L 89/00; C08L 99/00
USPC .......................................................... 523/351
See application file for complete search history.

(56) References Cited

U.S. PATENT DOCUMENTS

| | | |
|---|---|---|
| 5,032,512 A | 7/1991 | Witholt et al. |
| 5,145,779 A | 9/1992 | Pometto et al. |
| 5,212,219 A | 5/1993 | Griffin |
| 5,316,847 A | 5/1994 | Suominen |
| 5,378,738 A | 1/1995 | Deguchi et al. |
| 5,426,047 A | 6/1995 | Ito et al. |
| 6,312,578 B1 | 11/2001 | Canivenc et al. |
| 6,429,006 B1 | 8/2002 | Porro et al. |
| 7,465,575 B2 | 12/2008 | Nilsson |
| 7,534,597 B2 | 5/2009 | Hause et al. |
| 7,960,154 B1 | 6/2011 | Nakajima et al. |
| 8,137,953 B2 | 3/2012 | Miller et al. |
| 8,476,056 B2 | 7/2013 | Hoang et al. |

(Continued)

FOREIGN PATENT DOCUMENTS

| | | |
|---|---|---|
| CN | 1322045 | 6/2007 |
| CN | 101 457 218 | 6/2009 |

(Continued)

OTHER PUBLICATIONS

Written Opinion in International Application No. PCT/EP2017/062028, dated Jun. 30, 2017, pp. 1-5.
Matsuda, E. et al. "Gene Cloning and Molecular Characterization of an Extracellular Poly($_L$-Lactic Acid) Depolymerase from *Amycolatopsis* sp. Strain K104-1" *Journal of Bacteriology*, Nov. 2005, pp. 7333-7340, vol. 187, No. 21.
Database WPI, Accession No. 2009-K99963, Jun. 17, 2009, pp. 1-2, XP-002690934.

(Continued)

*Primary Examiner* — Hannah J Pak
(74) *Attorney, Agent, or Firm* — Saliwanchik, Lloyd & Eisenschenk

(57) ABSTRACT

The present invention relates to a masterbatch composition comprising high concentration of biological entities having a polymer-degrading activity and uses thereof for manufacturing biodegradable plastic articles.

15 Claims, 4 Drawing Sheets

(56) References Cited

U.S. PATENT DOCUMENTS

Figure 1A:
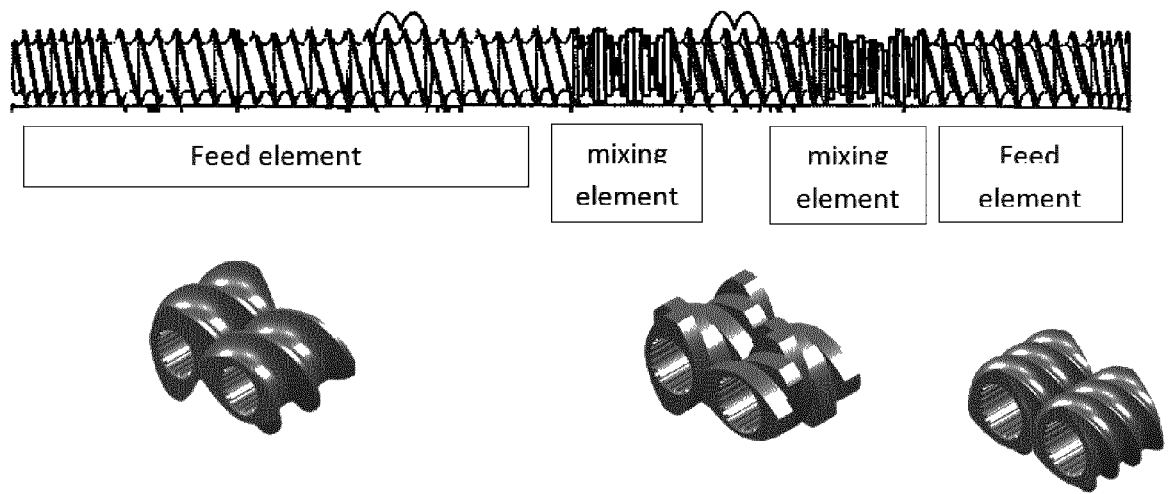

| | | |
|---|---|---|
| 8,614,076 B2 | 12/2013 | Wada et al. |
| 8,859,260 B2 | 10/2014 | Sawai et al. |
| 9,476,073 B2 | 10/2016 | Boisart |
| 9,528,132 B2 | 12/2016 | Mazzoli et al. |
| 10,124,512 B2 | 11/2018 | Boisart et al. |
| 10,287,561 B2 | 5/2019 | Alvarez et al. |
| 10,385,183 B2 | 8/2019 | Maille |
| 2005/0261465 A1 | 11/2005 | Nagarajan |
| 2006/0106120 A1 | 5/2006 | Abe et al. |
| 2008/0242784 A1* | 10/2008 | Ganesan ............ C08G 63/19 524/413 |
| 2011/0008855 A1 | 1/2011 | Park et al. |
| 2011/0200771 A1 | 8/2011 | Barclay |
| 2011/0245057 A1 | 10/2011 | Scoledes et al. |
| 2011/0319588 A1 | 12/2011 | Coupin et al. |
| 2012/0184005 A1 | 7/2012 | Ferreira et al. |
| 2013/0274373 A1 | 10/2013 | Yoshikawa et al. |
| 2014/0303278 A1 | 10/2014 | Ferreira et al. |
| 2015/0056673 A1 | 2/2015 | Boisart |
| 2015/0167030 A1 | 6/2015 | Mazzoli et al. |
| 2015/0290840 A1 | 10/2015 | Boisart et al. |
| 2016/0280881 A1 | 9/2016 | Boisart et al. |
| 2017/0114205 A1 | 4/2017 | Maille |
| 2017/0313998 A1 | 11/2017 | Alvarez et al. |
| 2017/0349723 A1 | 12/2017 | Ferreira et al. |
| 2018/0051264 A1 | 2/2018 | Li et al. |
| 2018/0142097 A1 | 5/2018 | Guemard et al. |
| 2019/0002933 A1 | 1/2019 | Dusseaux et al. |
| 2019/0218360 A1 | 7/2019 | Dusseaux et al. |
| 2019/0225954 A1 | 7/2019 | Tournier et al. |
| 2019/0233803 A1 | 8/2019 | Topham et al. |

FOREIGN PATENT DOCUMENTS

| | | |
|---|---|---|
| CN | 102250379 | 11/2011 |
| CN | 102675712 | 9/2012 |
| CN | 103980535 | 8/2014 |
| EP | 0 421 413 | 4/1991 |
| EP | 0 738 752 | 10/1996 |
| EP | 1 548 053 | 6/2005 |
| EP | 2 013 280 | 1/2009 |
| EP | 2 348 122 | 7/2011 |
| EP | 2 377 945 | 10/2011 |
| EP | 2 471 910 | 7/2012 |
| EP | 2 626 386 | 8/2013 |
| JP | 2000-506442 | 5/2000 |
| JP | 2002-293982 | 10/2002 |
| JP | 2002-320499 | 11/2002 |
| JP | 2002 362578 | 12/2002 |
| JP | 2003-079388 | 3/2003 |
| JP | 2003-128835 | 5/2003 |
| JP | 2004 058010 | 2/2004 |
| JP | 2004-290130 | 10/2004 |
| JP | 2004 292705 | 10/2004 |
| JP | 2007 319092 | 12/2007 |
| JP | 2012 149273 | 8/2012 |
| JP | 2012-152171 | 8/2012 |
| JP | 2013 000099 | 1/2013 |
| JP | 5 630597 | 11/2014 |
| KR | 20110045975 | 5/2011 |
| WO | WO 89/10381 | 11/1989 |
| WO | WO 2005/026245 | 3/2005 |
| WO | WO 2010/012805 | 2/2010 |
| WO | WO 2010/081887 | 7/2010 |
| WO | WO 2011/039489 | 4/2011 |
| WO | WO 2013/144239 | 10/2013 |
| WO | WO 2014/079844 | 5/2014 |
| WO | WO 2014/122698 | 8/2014 |
| WO | WO 2014/167518 | 10/2014 |
| WO | WO 2014/167562 | 10/2014 |
| WO | WO 2015/067619 | 5/2015 |
| WO | WO 2015/097104 | 7/2015 |
| WO | WO 2015/173265 | 11/2015 |
| WO | WO 2016/198650 | 12/2016 |
| WO | WO 2016/198652 | 12/2016 |
| WO | WO 2017/108577 | 6/2017 |
| WO | WO 2017/198786 | 11/2017 |

OTHER PUBLICATIONS

Database WPI, Accession No. 2008-F66138, Dec. 13, 2007, pp. 1-2, XP-002690935.

Wang, Z.-Y. et al. "Gene Cloning and Characterization of a Poly($_L$-Lactic Acid) Depolymerase from *Pseudomonas* sp. Strain DS04-T" *J Polym Environ*, Aug. 28, 2011, pp. 827-833, vol. 19, No. 4.

Akutsu-Shigeno, Y. et al. "Cloning and Sequencing of a Poly($_{DL}$-Lactic Acid) Depolymerase Gene from *Paenibacillus amylolyticus* Strain TB-13 and Its Functional Expression in *Escherichia coli*" *Applied and Environmental Microbiology*, May 2003, pp. 2498-2504, vol. 69, No. 5.

Petrov, K. et al. "$_L$(+)-Lactic acid production from starch by a novel amylolytic *Lactococcus lactis* subsp. *lactis* 884" *Food Microbiology*, Jun. 2008, pp. 550-557, vol. 25.

Currently pending claims of U.S. Appl. No. 14/443,524, 2016, pp. 1-4.

Bernard, N. et al. "Cloning of the D-lactate dehydrogenase gene from *Lactobacillus delbrueckii* subsp. *bulgaricus* by complementation in *Escherichia coli*" *FEBS*, Sep. 1991, pp. 61-64, No. 1.

Wieczorek, A. et al. "Engineering the cell surface display of cohesins for assembly of cellulosome-inspired enzyme complexes on *Lactococcus lactis*" *Microbial Cell Factories*, Sep. 2010, pp. 1-13, Vo. 9, No. 69.

Wieczorek, A. et al. "Effects of synthetic cohesin-containing scaffold protein architecture on binding dockerin-enzyme fusions on the surface of *Lactococcus lactis*" *Microbial Cell Factories*, 2012, pp. 1-13, vol. 160, No. 11.

Koukiekolo, R. et al. "Degradation of Corn Fiber by *Clostridium cellulovorans* Cellulases and Hemicellulases and Contribution of Scaffolding Protein CbpA" *Applied and Environmental Microbiology*, Jul. 1, 2005, pp. 3504-3511, vol. 71, No. 7.

Cha, J. et al. "Effect of Multiple Copies of Cohesins on Cellulase and Hemicellulase Activities of *Clostridium cellulovorans* Minicellulosomes" *Journal of Microbiology and Biotechnology*, 2007, pp. 1782-1788, vol. 17, No. 11.

Kataeva, I. et al. "Interaction between *Clostridium thermocellum* endoglucanase CelD and polypeptides derived from the cellulosome-integrating protein CipA: stoichiometry and cellulolytic activity of the complexes" *Biochemical Journal*, 1997, pp. 617-624, vol. 326, No. 2.

Wen, F. et al. "Yeast Surface Display of Trifunctional Minicellulosomes for Simultaneous Saccharification and Fermentation of Cellulose to Ethanol" *Applied and Environmental Microbiology*, Feb. 1, 2010, pp. 1251-1260, vol. 76, No. 4.

Hyeon, J. E. et al. "Production of minicellulosomes for the enhanced hydrolysis of cellulosic substrates by recombinant *Corynebacterium glutamicum*" *Enzyme and Microbial Technology*, 2011, pp. 371-377, vol. 48.

Sun, J. et al. "Direct Conversion of Xylan to Ethanol by Recombinant *Saccharomyces cerevisiae* Strains Displaying an Engineered Minihemicellulosome" *Applied and Environmental Microbiology*, Jun. 2012, pp. 3837-3845, vol. 78, No. 11.

Database EMBL [Online] Accession No. HC441374, "Sequence 9 from Patent WO2010012805" Feb. 20, 2010, pp. 1-3, XP-002697306.

Database Geneseq [Online] Accession No. AZM34659, "*Clostridium* sp. Cellulose-binding protein-A (CbpA) DNA SEQ: 6" Oct. 13, 2011, p. 1, XP-002697307.

Written Opinion in International Application No. PCT/EP2013/061413, dated Aug. 5, 2013, pp. 1-7.

Devos, D. et al. "Practical Limits of Function Prediction" *Proteins: Structure, Function and Genetics*, 2000, pp. 98-107, vol. 41.

Whisstock, J. C. et al. "Prediction of protein function from protein sequence and structure" *Quarterly Reviews of Biophysics*, 2003, pp. 307-340, vol. 36, No. 3.

Witkowski, A. et al. "Conversion of a β-Ketoacyl Synthase to a Malonyl Decarboxylase by Replacement of the Active-Site Cysteine with Glutamine" *Biochemistry*, 1999, pp. 11643-11650, vol. 38.

(56) References Cited

OTHER PUBLICATIONS

Kisselev, L. "Polypeptide Release Factors in Prokaryotes and Eukaryotes: Same Function, Different Structure" *Structure*, Jan. 2002, pp. 8-9, vol. 10.
Database WPI, Accession No. 2005-262580, Mar. 24, 2005, pp. 1-3, XP-002690554.
Database WPI, Accession No. 2004-751104, Oct. 21, 2004, pp. 1-2, XP-002690555.
Currently pending claims of U.S. Appl. No. 14/387,285, 2014, pp. 1-3.
Yoshida, S. et al. "A bacterium that degrades and assimilates poly(ethylene terephthalate)" *Science*, Mar. 11, 2016, pp. 1196-1199, vol. 351.
Demirel, B. et al. "Crystallization Behavior of PET Materials" *BAU Fen Bil. Enst. Dergisi Cilt*, 2011, pp. 26-35, vol. 13, No. 1.
Kyrikou, I. et al. "Biodegradation of Agricultural Plastic Films: A Critical review" *J Polym Environ*, 2007, pp. 125-150, vol. 15.
Chen, S. et al. "Identification and Characterization of Bacterial Cutinase" *The Journal of Biological Chemistry*, Sep. 19, 2008, pp. 25854-25862, vol. 238, No. 38.
Ronkvist, A. M. et al. "Cutinase-Catalyzed Hydrolysis of Poly(ethylene terephthalate)" *Macromolecules*, 2009, pp. 5128-5138, vol. 42.
Nabil, H. et al. "Recycled Polyethylene Terephthalate Filled Natural Rubber Compounds: Effects of Filler Loading and Types of Matrix" *Journal of Elastomers and Plastics*, 2011, pp. 1-21, vol. 00-2011.
Bartolome, L. et al. "Recent Developments in the Chemical Recycling of PET" Material Recycling—Trends and Perspectives, Mar. 16, 2012, pp. 1-21.
Arutchelvi, J. et al. "Biodegradation of polyethylene and polypropylene" *Indian Journal of Biotechnology*, Jan. 2008, pp. 9-22, vol. 7.
Iwamoto, A. et al. "Enzymatic degradation of plastics containing polycaprolactone" *Polymer Degradation and Stability*, Jan. 1, 1994, pp. 205-213, vol. 45.
Mueller, R.-J. "Biological degradation of synthetic polyesters—Enzymes as potential catalysts for polyester recycling" *Process Biochemistry*, 2006, pp. 2124-2128, vol. 41, No. 10.
Written Opinion in International Application No. PCT/EP2014/073742, dated Aug. 8, 2015, pp. 1-5.
Herrero Acero, E. et al. "Enzymatic Surface Hydrolysis of PET: Effect of Structural Diversity on Kinetic Properties of Cutinases from *Thermobifida*" *Macromolecules*, 2011, pp. 4632-4640, vol. 44, No. 12.
Herrero Acero, E. et al. "Surface Engineering of a Cutinase From *Thermobifida cellulosilytica* for Improved Polyester Hydrolysis" *Biotechnology & Bioengineering*, Oct. 2013, pp. 2581-2590, vol. 110, No. 10.
Shah, A. A. et al. "Degradation of aliphatic and aliphatic-aromatic co-polyesters by depolymerases from *Roseateles depolymerans* strain TB-87 and analysis of degradation products by LC-MS" *Polymer Degradation and Stability*, Oct. 16, 2013, pp. 2722-2729, vol. 98, No. 12.
Written Opinion in International Application No. PCT/EP2015/060521, dated Jul. 20, 2015, pp. 1-6.
Wikipedia, https://web.archive.org/web/20130424032652/https://en.wikipedia.org/wiki/Polyethylene_terephthalate, archived Apr. 24, 2013, accessed Aug. 13, 2018, pp. 1-13.
Sukkhum, S. et al. "A novel poly ($_L$-lactide) degrading actinomycetes isolated from Thai forest soil, phylogenic relationship and the enzyme characterization" *The Journal of General and Applied Microbiology*, 2009, pp. 459-467, vol. 55, No. 6.
Sukkhum, S. et al. "Poly($_L$-Lactide)-Degrading Enzyme Production by *Actinomadura keratinilytica* T16-1 in 3 L Airlift Bioreactor and Its Degradation Ability for Biological Recycle" *Journal of Microbiology and Biotechnology*, Jan. 28, 2012, pp. 92-99, vol. 22, No. 1.
Written Opinion in International Application No. PCT/EP2015/074222, dated Feb. 1, 2016, pp. 1-5.
Niaounakis, 2013. Chapter 4: Disposal. Biopolymers Reuse, Recycling, and Disposal. A Volume in Plastics Design Library, a PDL Handbook Series. ISBN 978-1-4557-3145-9, published by Elsevier Inc, pp. 107-150.
Sugimori, Mar. 2013. Protease, washing agent containing the protease, and method of manufacturing the washing agent. EMBL AB809463, pp. 1-2.
Albertsson, A.-C. et al. "Chemistry and biochemistry of polymer biodegradation" *Chemistry and Technology of Biodegradable Polymers*, Jan. 1, 1994, pp. 7-17, Section 2.
Database WPI [Online] Accession No. 2012-Q50933, Sep. 9, 2012, p. 1, XP-002740253.
Database WPI [Online] Accession No. 2004-046313, dated May 8, 2003, pp. 1-2, XP-002740254.
Written Opinion in International Application No. PCT/EP2015/080557, dated Feb. 3, 2016, pp. 1-6.
Gouda, M. K. et al. "Production of a Polyester Degrading Extracellular Hydrolase from *Thermomonospora fusca*" *Biotechnology Progress*, Sep. 2002, pp. 927-934, vol. 18, No. 5.
Oda, Y. et al. "Degradation of Polylactide by Commercial Proteases" *Journal of Polymers and the Environment*, Jan. 2000, pp. 29-32, vol. 8, No. 1.
Written Opinion in International Application No. PCT/EP2016/055348, dated Jun. 2, 2016, pp. 1-6.
Database UniProt [Online] Accession No. I0LED3, Jun. 13, 2012, pp. 1-2, XP-002743807.
Database Geneseq [Online] Accession No. BAJ28992, Jan. 31, 2013, pp. 1-10, XP-002743803.
Database Geneseq [Online] Accession No. BAJ28991, Jan. 31, 2013, pp. 1-2, XP-002743804.
Database UniProt [Online] Accession No. F4F956, Jun. 28, 2011, pp. 1-2, XP-002743805.
Database UniProt [Online] Accession No. A8LWF7, Dec. 4, 2007, p. 1-2, XP-002743806.
Written Opinion in International Application No. PCT/EP2016/063373, dated Aug. 8, 2017, pp. 1-7.
Okino, S. et al. "Production of D-lactic acid by *Corynebacterium glutamicum* under oxygen deprivation" *Applied Microbiology and Biotechnology*, Jan. 10, 2008, pp. 449-454, vol. 78, No. 3.
Database WPI [Online] Accession No. 2012-K88398, Jan. 27, 2011, pp. 1-2, XP-002759107.
Written Opinion in International Application No. PCT/EP2016/081205, dated Jun. 1, 2017, pp. 1-19.
Currently pending claims of U.S. Appl. No. 16/302,107, 2018, pp. 1-4.
Currently pending claims of U.S. Appl. No. 16/064,494, 2018, pp. 1-3.
Written Opinion in International Application No. PCT/EP2016/063369, dated Aug. 1, 2016, pp. 1-6.
Claims pending in U.S. Appl. No. 16/470,295, 2019, pp. 1-4.

* cited by examiner

MASTERBATCH COMPOSITION COMPRISING A HIGH CONCENTRATION OF BIOLOGICAL ENTITIES

CROSS-REFERENCE TO RELATED APPLICATION

This application is the U.S. national stage application of International Patent Application No. PCT/EP2016/063369, filed Jun. 10, 2016.

FIELD OF THE INVENTION

The present invention relates to a novel masterbatch composition comprising a high concentration of biological entities. The invention also relates to a process for producing such masterbatch composition, and the use thereof for the production of plastic articles.

BACKGROUND OF THE INVENTION

Plastics are inexpensive and durable materials, which are employed to manufacture a variety of products that find uses in a wide range of applications. As a consequence, the production of plastics has increased dramatically over the last decades. A large part of these plastics are used for single-use disposable applications, or for short-lived products (such as bags, packaging including trays, containers, bottles, agricultural films, etc.) that are discarded within a year of manufacture. Because of the durability of the polymers involved and their high resistance to biodegradation (due to high molecular mass values, hydrophobicity and crystallinity), substantial quantities of plastics are piling up in landfill sites and in natural habitats, generating increasing environmental problems worldwide.

To answer these problems, different physical, chemical and/or biochemical approaches have been developed to reduce the biodegradation resistance of polymers and to increase their biodegradation rate. For example, biodegradable plastic products have been developed. However, the environmental degradation conditions are not optimal for such biodegradable plastics and their degradation generally takes place partially.

Recently, a novel plastic material has been developed that contains a small amount of biological entities having a polymer-degrading activity. The biological entities are interestingly able to degrade at least one polymer of said plastic material. The process for manufacturing such plastic material has been described in patent application WO 2013/093355. The plastic material obtained by this process contains biological entities dispersed in a polymer, and is directly usable through an extrusion die for producing plastic articles having improved biodegradability.

The present invention provides improved methods and compositions for producing plastic articles with increased biodegradability. The inventors have developed masterbatch compositions containing high concentrations of biological entities dispersed in a carrier material and they have shown that such compositions may be used to produce plastic materials with remarkable properties. In particular, the compositions and methods of the invention allow the production of plastic articles with an improved dispersion and distribution rate of biological entities in the plastic article, thus leading to an improved control of the biodegradability. Furthermore, the methods of the invention can be used in standard operations of plastics processing and do not impair the mechanical properties of the resulting plastic articles.

SUMMARY OF THE INVENTION

The present invention relates to novel masterbatch compositions comprising a high concentration of biological entities embedded into a carrier material. The invention also relates to a process for producing such masterbatch compositions and to the uses thereof, particularly in a process for the production of plastic articles. Surprisingly, the inventors have discovered that high amounts of biological entities may be introduced into a carrier material, even during a mixing step performed at elevated temperature, and that the biological entities in the resulting masterbatch retain a polymer-degrading activity allowing the efficient production of plastic articles having improved biodegradability. Furthermore, the present invention shows that an effective degrading activity is present in the plastic article even when the masterbatch is introduced into the plastic by mixing at an elevated temperature i.e., after two successive heating of the biological entities (i.e., during the process of manufacturing the masterbatch and during uses of said masterbatch to produce plastics). The masterbatch composition and methods of the invention thus offer remarkable advantage for the manufacture of improved plastic articles under industrial conditions.

It is therefore an object of the invention to provide a masterbatch composition comprising a carrier material and biological entities having a polymer-degrading activity, wherein the carrier material represents between 10% and 89% by weight of the total weight of the masterbatch composition.

The masterbatch composition preferably comprises from 11% to 90% by weight of biological entities, based on the total weight of the masterbatch composition.

It is another object of the invention to provide a process for preparing a masterbatch composition, comprising a step (a) of mixing 11% to 90% by weight of biological entities having a polymer-degrading activity, with 10% to 89% by weight of a carrier material and, optionally, a step (b) of conditioning said mixture of step (a) in an solid form.

The invention also relates to the use of such masterbatch composition for the manufacture of plastic articles.

Additionally, the invention relates to a plastic article made from such masterbatch composition, wherein the biological entities are suitable for degrading at least one polymer of the plastic article.

It is also an object of the invention to provide a method for manufacturing a plastic article comprising at least one polymer, the method comprising:
A. providing a masterbatch composition as defined above, wherein the biological entities in said masterbatch are suitable for degrading said at least one polymer, and
B. introducing said masterbatch composition in said polymer during production of said plastic article.

It is also another object of the invention to provide a method for increasing biodegradability of a plastic article comprising at least one polymer, said method comprising mixing the polymer with a masterbatch composition of the invention, wherein the biological entities of the masterbatch composition degrade said polymer, and further manufacturing a plastic article with said mixture.

LEGEND TO THE FIGURES

Figure 1B:
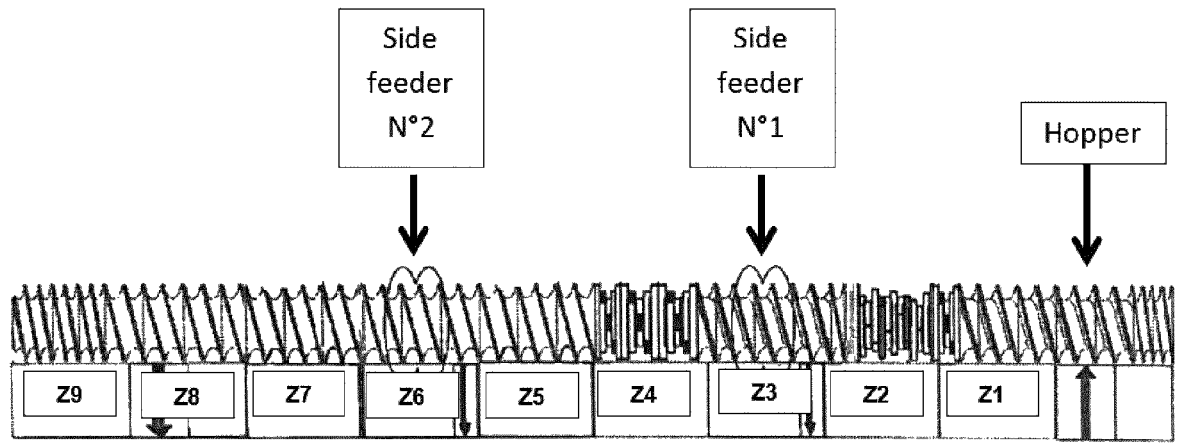

FIGS. 1A and 1B: Schematic representation of the twin-screw of an extruder that may be used for producing a masterbatch composition of the invention (FIG. 1A: Repartition of the feed and mixing elements; FIG. 1B: Repartition of the successive heating zones Z1-Z9).

Figure 2:
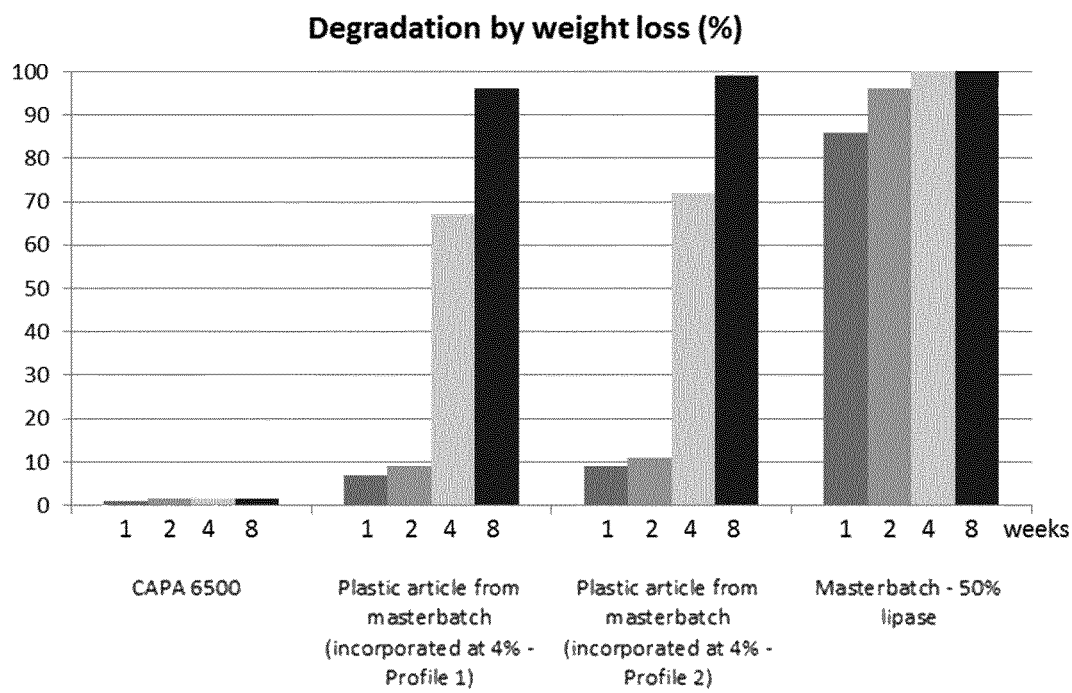

FIG. 2: Results for the biodegradation tests of a masterbatch composition of the invention in a solid form (comprising 50% by weight of polycaprolactone and 50% by weight of a formulation of lipase PS); a commercial polycaprolactone; and two different plastic articles of the invention, obtained by mixing 4% by weight of the masterbatch composition with said commercial polycaprolactone.

Figure 3:
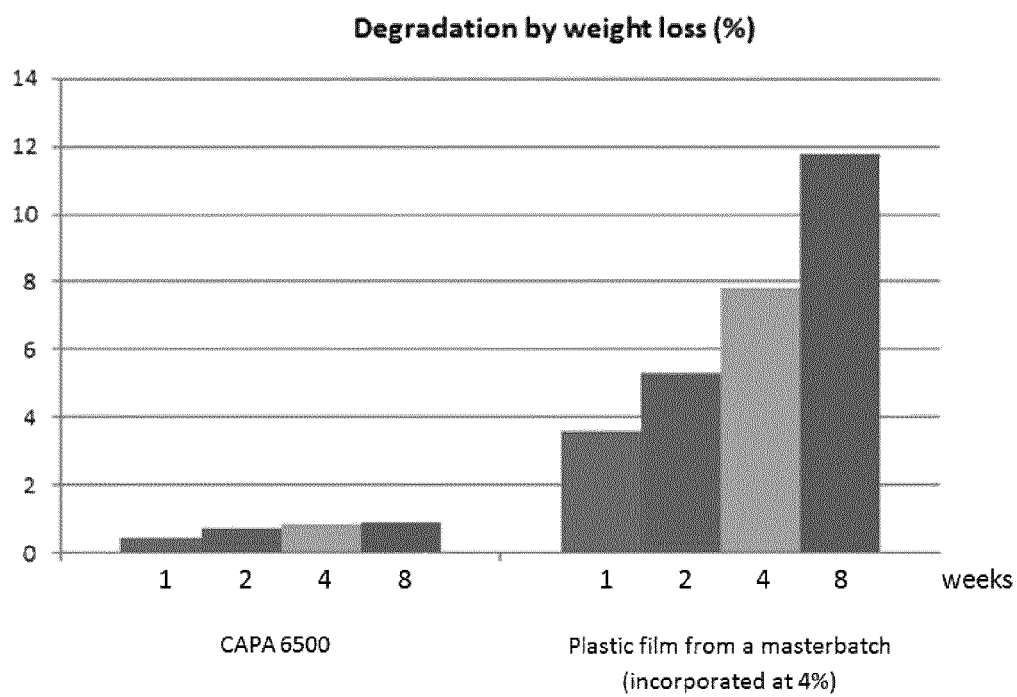

FIG. 3: Results for the biodegradation test of a commercial polycaprolactone and a plastic film of the invention, obtained by mixing 4% by weight of a masterbatch composition of the invention (50% by weight of polycaprolactone and 50% by weight of a formulation of lipase PS) with said commercial polycaprolactone.

Figure 4:
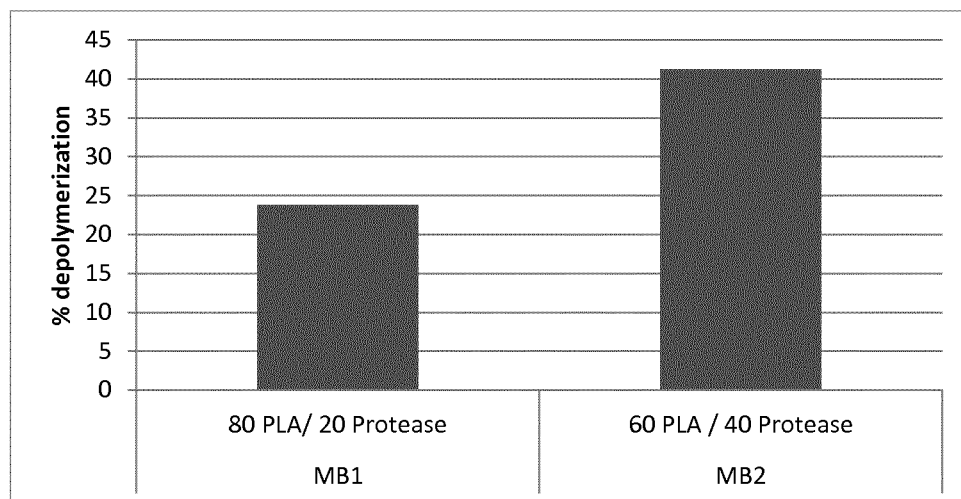

FIG. 4: Results for the degradation test of masterbatchs (MB1, MB2) according to the invention containing PLA and protease; both masterbatchs show a high degradation rate (24% and 41%, respectively); the masterbatch containing 40% of biological entities exhibits a degradation rate twice higher than the masterbatch containing 20% of biological entities.

Figure 5:
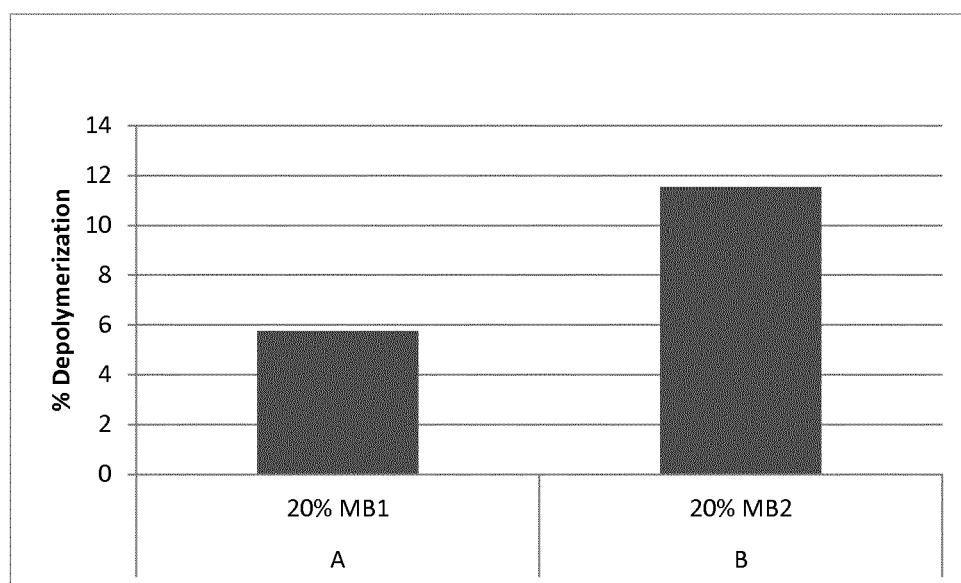

FIG. 5: Results for the degradation test of plastic articles (A, B) made with masterbatchs of the invention, which confirm that the degrading activity of biological entities is maintained in the final plastic articles.

Figure 6:
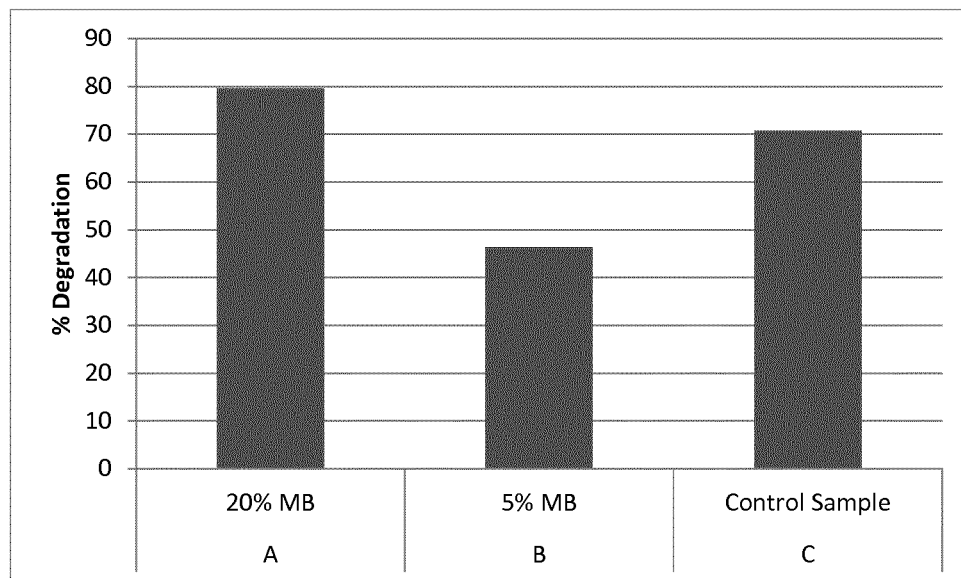

FIG. 6: Results for the degradation test of plastic articles A (8% protease) and B (2% protease) made with masterbatchs of the invention compared to plastic article C (8% protease) wherein biological entities have been incorporated directly to the polymer of the plastic article; the results confirm that the plastic article A, produced from masterbatch of the invention, has a better biodegradability compared to plastic article C, made by adding biological entities directly to the polymer of the plastic article.

Figure 7:
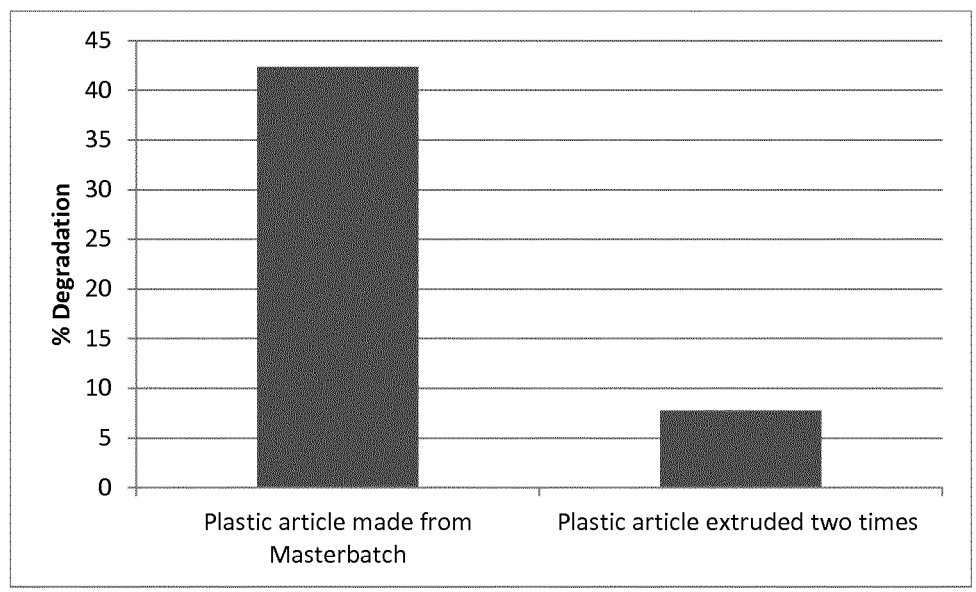

FIG. 7: Comparative results of degradation of a plastic article made with a masterbatch of the invention and a control plastic article, wherein biological entities have been added directly to the polymer of the plastic article. The results confirm that the plastic article produced with a masterbatch has a better biodegradability compared to the control plastic article.

DETAILED DESCRIPTION OF THE INVENTION

The present invention relates to novel compositions and methods for producing improved plastic materials and articles. More particularly, the invention provides novel masterbatch compositions comprising a high concentration of biological entities and a carrier material. The invention shows that such masterbatch compositions can be used to prepare improved biodegradable plastic articles having suitable dispersion and distribution rate of active biological entities. Furthermore, said masterbatch may be used as a classical masterbatch to manufacture plastic articles with an integrated polymer-degrading activity, despite the successive heat exposures.

Definitions

The present disclosure will be best understood by reference to the following definitions.

As used herein, the term "masterbatch composition" designates a concentrated mixture of selected ingredients (e.g., active agents, additives, etc.) that can be used for introducing said ingredients into plastic articles or materials in order to impart desired properties thereto. Masterbatch compositions may be solid or liquid. Masterbatch compositions allow the processor to introduce selected ingredients economically during plastic manufacturing process. Generally, the masterbatch composition is used with a base polymer to produce a final plastic article having a desired amount of selected ingredients. Preferably, masterbatch compositions of the invention contain at least 10% by weight of active ingredients, more preferably of biological entities having a polymer-degrading activity.

Within the context of the invention, the terms "plastic article" or "plastic product" are used interchangeably and refer to any item made from at least one polymer, such as plastic sheet, tube, rod, profile, shape, massive block, fiber, etc. Preferably, the plastic article is a manufactured product, such as a rigid or flexible packaging, agricultural films, bags and sacks, disposable items or the like. Preferably, the plastic article comprises a mix of semi-crystalline and/or amorphous polymers, or semi-crystalline polymers and additives. The plastic articles may contain additional substances or additives, such as plasticizers, mineral or organic fillers.

The term "plastic material" refers typically to a raw mixture of polymer(s) and additional compounds (e.g., additives, enhancers, etc.) before any shaping or conditioning step.

A "polymer" refers to a chemical compound or mixture of compounds whose structure is constituted of multiple repeating units linked by covalent chemical bonds. Within the context of the invention, the term "polymer" includes natural or synthetic polymers, comprising a single type of repeating unit (i.e., homopolymers) or different types of repeating units (i.e., block copolymers and random copolymers). As an example, synthetic polymers include polymers derived from petroleum oil or biobased polymers, such as polyolefins, aliphatic or aromatic polyesters, polyamides, polyurethanes and polyvinyl chloride. Natural polymers include lignin and polysaccharides, such as cellulose, hemicellulose, starch and derivatives thereof that may or may not be plasticized.

In the context of the invention, the term "carrier material" refers to any material that is capable of carrying a high amount of selected ingredients, including biological entities, and to be further incorporated in a plastic article. Advantageously, the carrier material is compatible across a broad range of polymers or for particular polymers usually used for manufacturing plastic articles. Preferably, the carrier material is compatible with the main polymer that will incorporate the masterbatch. The carrier material generally comprises mineral or organic fillers, or natural or synthetic polymers, or any combination thereof.

In the context of the invention, the term "filler" refers to a substance that is incorporated to a plastic material and/or to a plastic product to reduce the costs thereof or, optionally, improve the physical properties thereof (e.g., its hardness, stiffness or strength). Fillers can be inactive (i.e., inert) or active material, and may form chemical bonds with the components of the plastic material or product. Fillers can be synthetic, natural or modified fillers. Fillers may comprise mineral and/or organic fillers. Examples of mineral fillers used in the plastic manufacturing industry include without limitation calcium carbonate (limestone), magnesium silicates (talc), calcium sulfate (gypsum), mica, calcium silicate, barium sulphate and kaolin (China clay). Examples of organic fillers include without limitation starch, cellulose or hemi-cellulose, cereal flour, wood flour, tree bark flour, nut flours, hemp fibers, chicken feathers, and rice hulls.

As used herein, the term "biological entities" designates active enzymes or enzyme-producing microorganisms, such as sporulating microorganisms, as well as combinations or formulations thereof. For instance, "biological entities" may refer to pure enzymes or microorganisms as well as to formulations containing enzymes and/or microorganisms and a diluent or carrier, such as stabilizing and/or solubilizing component(s), including water, glycerol, sorbitol, dextrin, including maltodextrin and/or cyclodextrin, starch, glycol such as propanediol, salt, etc. The biological entities may be in solid (e.g., powder) or liquid form.

As used herein, the term "by weight" refers to the ratio based on the total weight of the considered composition or product.

In the context of the invention, the term "about" refers to a margin of +/−5%, preferably of +/−1%, or within the tolerance of a suitable measuring device or instrument.

Biological Entities

The present invention relates to a masterbatch composition comprising a carrier material and biological entities having a polymer-degrading activity, wherein said biological entities represent more than 11% by weight of the masterbatch composition. According to the invention, such masterbatch composition exhibits a polymer-degrading activity and may be used to confer improved biodegradability on plastic materials and articles.

In a particular embodiment, the masterbatch composition comprises more than 15% by weight of biological entities, preferably more than 20%, more preferably more than 30%, and even more preferably more than 40%. Advantageously, the masterbatch composition comprises between 11% and 90% by weight of biological entities, preferably between 20% and 80%, more preferably between 30% and 70%, and even more preferably between 40% and 60% by weight of biological entities. In a preferred embodiment, the masterbatch composition comprises about 50% by weight of biological entities.

In a preferred embodiment, the biological entities comprise at least an enzyme with polymer-degrading activity and/or at least a microorganism expressing, and optionally excreting, an enzyme having a polymer-degrading activity.

In a particular embodiment, the biological entities comprise or consist in at least an enzyme with synthetic polymer-degrading activity and/or at least a microorganism expressing, and optionally excreting, an enzyme having a synthetic polymer-degrading activity. Preferably, the biological entities comprise or consist in at least an enzyme with polyester-degrading activity and/or at least a microorganism expressing, and optionally excreting, an enzyme having a polyester-degrading activity.

Examples of suitable enzymes having a polymer-degrading activity for use in the invention include, without limitation, depolymerase, esterase, lipase, cutinase, hydrolase, protease, polyesterase, oxygenase and/or oxidase such as laccase, peroxidase or oxygenase. The enzymes may be in pure or enriched form, or in mixture with other excipients or diluents. A combination of enzymes may be used as well.

In an alternative embodiment, the biological entities comprise microorganisms that produce such enzymes, either naturally or as a result of particular engineering (e.g., recombinant microorganisms). Preferred examples of suitable microorganisms include, without limitation, bacteria, fungi and yeasts. In an embodiment, the biological entities comprise sporulating microorganisms and/or spores thereof.

In a particular embodiment, the biological entities comprise enzymes encapsulated in nanocapsules consisting of the same material as the carrier material of the masterbatch, enzymes encapsulated in cage molecules, and enzymes aggregated together. In another particular embodiment, the biological entities comprise enzymes encapsulated in nanocapsules in a material different of the carrier material of the masterbatch. Particularly such material is chosen among material compatible and/or miscible with the carrier material of the masterbatch. The term "cage molecule" designates a molecule that can be inserted into the structure of said enzymes to stabilize them and to make them resistant to high temperatures. Encapsulation techniques are well known to those skilled in the art and include, for instance, nanoemulsions.

The biological entities may be supplied in a liquid or solid form. For instance, the biological entities may be in a powder form. To this aim, the biological entities may be dried or dehydrated. Methods for drying or dehydrating biological entities such as microorganisms or enzymes are well known to the one skilled in the art and include, without limitation, lyophilisation, freeze-drying, spray-drying, supercritical drying, down-draught evaporation, thin-layer evaporation, centrifugal evaporation, conveyer drying, fluidized bed drying, drum drying or any combination thereof.

In a particular embodiment, the biological entities used to prepare the masterbatch are a formulation of enzymes and/or microorganisms mixed with a diluent or carrier, such as stabilizing and/or solubilizing component(s). For instance, the formulation may be a solution comprising enzymes and/or microorganisms in suspension in water, and optionally additional components, such as glycerol, sorbitol, dextrin, starch, glycol such as propanediol, salt, etc. Alternatively, the formulation may be a powder comprising enzymes and/or microorganisms in powder form mixed with a stabilizing powder, such as maltodextrin.

In a particular embodiment, the biological entities comprise the culture supernatant of a polymer-degrading microorganism. In this regard, a particular object of the invention relates to a liquid masterbatch composition as defined above which comprises between 20% and 80%, more preferably between 30% and 70%, and even more preferably between 40% and 60% by weight of a culture supernatant of a polymer-degrading microorganism. The supernatant may be treated (e.g., mechanically or physically or chemically) to increase the concentration of enzymes and/or to remove other components such as DNA or cell debris.

Carrier Material

According to the invention, the masterbatch composition comprises between 10% and 89% by weight of carrier material, based on the total weight of the composition. In a particular embodiment, the carrier material represents less than 80% by weight, preferably less than 70%, and more preferably less than 60%. For instance, preferred masterbatch compositions of the invention comprise between 20% and 80% by weight of carrier material, preferably between 30% and 70%, more preferably between 40% and 60%. In a particular embodiment, the masterbatch composition comprises about 45% by weight of carrier material. The amount of carrier material in the masterbatch composition may be easily evaluated by techniques well known by a person skilled in the art, such as thermogravimetric analysis, or spectroscopy. It can easily be controlled during manufacturing of the masterbatch.

According to the invention, the carrier material is preferably selected from mineral or organic fillers, or natural or synthetic polymers, or any combination thereof.

In a particular embodiment, the carrier material comprises a polymer. The polymer may be selected from natural or synthetic polymers. Particularly, the masterbatch composition comprises a polymer that can be degraded by the biological entities of the masterbatch composition.

Natural polymers may be selected from the group of lignin, polysaccharides such as cellulose or hemi-cellulose, starch, chitin, chitosan and derivatives thereof or blends/mixtures thereof. In a particular embodiment, the natural polymers are plasticized (e.g., by a plasticizer such as water or glycerol) prior to their use for producing the masterbatch composition. Such plastifying step modifies the chemical structure of the natural polymers allowing their use through a plastic production process.

Synthetic polymers may be selected from the group consisting without limitation to polyolefins, aliphatic or semi-aromatic polyesters, polyamides, polyurethanes, or vinyl polymers and derivatives thereof or blends/mixtures of these materials.

Preferred polyolefins for use in the present invention include, without limitation, polyethylene (PE), polypropylene (PP), polymethylpentene (PMP), polybutene-1 (PB-1), polyisobutylene (PIB), ethylene propylene rubber (EPR), ethylene propylene diene monomer rubber (EPDM), cyclic olefin copolymer (COC) and derivatives or blends/mixtures thereof.

Preferred aliphatic polyesters for use in the invention include, without limitation, polylactic acid (PLA), poly(L-lactic acid) (PLLA), poly(D-lactic acid) (PDLA), poly(D,L-lactic acid) (PDLLA), PLA stereocomplex (scPLA), polyglycolic acid (PGA), polyhydroxyalkanoate (PHA), polycaprolactone (PCL), polybutylene succinate (PBS); and semi-aromatic polyetsers are selected from polyethylene terephthalate (PET), polytrimethylene terephthalate (PTT), polybutylene terephthalate (PBT), polyethylene isosorbide terephthalate (PEIT), polybutylene succinate adipate (PBSA), polybutylene adipate terephthalate (PBAT), polyethylene furanoate (PEF), poly(ethylene adipate) (PEA), polyethylene naphthalate (PEN), and derivatives or blends/mixtures thereof.

Preferred polyamide polymers (also called nylon) for use in the invention include without limitation, polyamide-6 or poly(β-caprolactam) or polycaproamide (PA6), polyamide-6,6 or poly(hexamethylene adipamide) (PA6,6), poly(11-aminoundecanoamide) (PA11), polydodecanolactam (PA12), poly(tetramethylene adipamide) (PA4,6), poly(pentamethylene sebacamide) (PA5,10), poly(hexamethylene azelaamide) (PA6,9), poly(hexamethylene sebacamide) (PA6,10), poly(hexamethylene dodecanoamide) (PA6,12), poly(m-xylylene adipamide) (PAMXD6), polyhexamethylene adipamide/polyhexamethyleneterephtalamide copolymer (PA66/6T), polyhexamethylene adipamide/polyhexamethyleneisophtalamide copolymer (PA66/6I) and derivatives or blends/mixtures thereof.

Preferred vinyl polymers include polystyrene (PS), polyvinyl chloride (PVC), polyvinyl chloride (PVdC), ethylene vinyl acetate (EVA), ethylene vinyl alcohol (EVOH), polyvinyl alcohol (PVOH) and derivatives or blends/mixtures of these materials.

In a particular embodiment, the carrier material of the masterbatch comprises at least one polymer that has a melting temperature below 180° C., and/or a glass transition temperature below 70° C., preferably selected from the group consisting of PLA, PCL, PBAT, PHA, PBS and EVA. Preferably, the carrier material of the masterbatch comprises at least one polymer that has a melting temperature below 120° C., and/or a glass transition temperature below 30° C., preferably selected from the group consisting of PCL, PBAT, and EVA.

In a particular embodiment, the masterbatch composition comprises a "universal" polymer, i.e., a polymer that is compatible with a broad range of polymers. Most often, known universal masterbatch compositions use ethylene vinyl acetate copolymer (EVA) as a carrier material.

In another embodiment, the carrier material comprises a filler. The filler can be selected from any conventional filler used in the plastic industry. The filler can be natural or synthetic. The filler can be selected from mineral or organic fillers. In a preferred embodiment, the mineral filler is chosen from the group consisting without limitation of calcite, carbonate salts or metal carbonate such as calcium carbonate (or limestone), potassium carbonate, magnesium carbonate, aluminium carbonate, zinc carbonate, copper carbonate, chalk, dolomite, silicate salts such as hydrous magnesium silicate such as talc or soapstone, calcium silicate (wollastonite), potassium silicate, magnesium silicates (talc), aluminium silicate (kaolin), or mix thereof such as mica, smectite such as montmorillonite, vermiculite, and palygorskite-sepiolite, sulphate salts such as barium sulfate, or calcium sulfate (gypsum), mica, hydroxide salt or metal hydroxide such as calcium hydroxide or potassium hydroxide (potash) or magnesium hydroxide or aluminium hydroxide or sodium hydroxide (caustic soda), hydrotalcite, metal oxide or oxide salts such as oxide of magnesium or oxide of calcium or oxide of aluminium or iron oxide or copper oxide, clay, asbestos, silica, graphite, carbon black, metal fibers or metal flakes, glass fibers, magnetic fillers, aramid fibers, ceramic fibers and derivatives thereof or blends/mixtures of these materials. In another preferred embodiment, the organic filler is chosen from the group consisting of wood flour, plant or vegetable flour such as cereal flour (corn flour, wheat flour, rice flour, soy bean flour, nutshell flour, clam shell flour, corn cob flour, cork flour, rice hull flour); saw dust; plant fibers such as flax fibers, wood fibers, hemp fibers, bamboo fibers, chicken feathers and derivatives thereof or blends/mixtures of these materials. Natural polymers can also be used as organic fillers, such as lignin, or polysaccharides such as cellulose or hemi-cellulose, starch, chitin, chitosan and derivatives or blends/mixtures of these materials. The type and exact quantity of fillers can be adapted by a person skilled in the art depending on the type of masterbatch composition and following guidance provided in the present application.

In a particular embodiment, the masterbatch composition comprises both polymer(s) and filler(s). For instance, the masterbatch composition preferably comprises more polymer(s) than filler(s). Reversely, the masterbatch composition may comprise more filler(s) than polymer(s).

Additional Compounds

The masterbatch composition may further comprise one or several additional compounds.

In particular, the masterbatch composition may further comprise one or more additives. Generally speaking, the additives are used in order to enhance specific properties in the final product (i.e., the final plastic article made with said masterbatch composition). For instance, the additives may be selected from the group consisting without limitation of plasticizers, coloring agents, processing aids, rheological agents, anti-static agents, anti-UV agents, toughening agents, anti-fogging agents, compatibilizers, slip agents, flame retardant agents, anti-oxidants, light stabilizers, oxygen scavengers, inks, adhesives, fertilizers, and phytosanitary products. Advantageously, the masterbatch composition comprises less than 20% by weight of such additives, preferably less than 10%, more preferably less than 5%, typically between 0.1 and 4% by weight of such additives.

In another particular embodiment, the masterbatch composition further comprises at least one pro-oxidant element, preferably selected from the group consisting without limitation of metal carboxylate such as cobalt, iron, manganese, nickel, or zinc. Advantageously, the masterbatch composition comprises less than 20% by weight of pro-oxidants, preferably less than 10%, more preferably less than 5%, typically between 0.1 and 4% by weight of such additives.

Masterbatch Compositions

It is an object of the invention to provide masterbatch compositions comprising high concentrations of active biological entities embedded in a carrier material. According to the invention, high amounts of active biological entities having a polymer-degrading activity are added to a carrier material in order to produce a composition wherein a polymer-degrading activity is present. The masterbatch compositions of the invention may be easily used for further preparing plastic articles or materials with improved degradability in environmental conditions.

The masterbatch compositions may be in solid form (e.g., powder or granulates) or in liquid form. Preferably, the masterbatch composition is in a solid physical form with a melt flow index comprised between 1 to 60. Such melt flow index may be measured by techniques known by a person skilled in the art such as capillary rheometers or melt flow rheometers. The form of the masterbatch composition may be advantageously adapted to the final purpose of said composition (e.g., the nature of the polymer, the kind of plastic product to be produced, etc.).

In the same way, the biological entities and amounts thereof may be adapted to the final plastic product.

In a particular embodiment, the masterbatch composition comprises, based on the total weight of the masterbatch composition:
  from 5 to 30% by weight of at least one polymer;
  from 5 to 30% by weight of at least one filler;
  from 30 to 70% by weight of biological entities having a polymer-degrading activity; and optionally
  at least one additive and/or one pro-oxidant.

In another particular embodiment, the masterbatch composition comprises, based on the total weight of the masterbatch composition:
  from 30 to 70% by weight of at least one polymer;
  from 5 to 30% by weight of at least one filler;
  from 20 to 40% by weight of biological entities having a polymer-degrading activity; and optionally
  at least one additive and/or one pro-oxidant.

In another embodiment, the masterbatch composition comprises, based on the total weight of the masterbatch composition:
  from 30 to 70% by weight of at least one polymer; and
  from 30 to 70% by weight of biological entities having a polymer-degrading activity; and optionally
  at least one additive and/or one pro-oxidant.

Particularly, said biological entities are able to degrade the polymer of the masterbatch composition.

In another embodiment, the masterbatch composition comprises, based on the total weight of the masterbatch composition:
  from 30 to 70% by weight of at least one filler; and
  from 30 to 70% by weight of biological entities having a polymer-degrading activity; and optionally
  at least one additive and/or one pro-oxidant.

In a specific embodiment, the invention relates to a masterbatch composition comprising from 30 to 70% by weight of a formulation of a lipase and from 30 to 70% by weight of polycaprolactone, preferably from 40 to 60% by weight of a formulation of lipase and from 40 to 60% by weight of polycaprolactone, more preferably about 50% by weight of a formulation of lipase and about 50% by weight of polycaprolactone.

In another embodiment, the masterbatch composition comprises from 15 to 60%, preferably from 15 to 50%, by weight of a formulation of protease (such as proteinase K or Savinase® or protease from *Actinomadura keratinilytica* or protease from *Laceyella sacchari* LP175) and from 50 to 85% by weight of PLA, preferably from 20 to 40% by weight of a formulation of protease and from 60 to 80% by weight of PLA.

In a particular embodiment, the masterbatch composition comprises from 15 to 45% by weight of a formulation of spores degrading PLA, from 25 to 65% by weight of PLA and from 10 to 50% by weight of wheat flour, preferably from 15 to 35% by weight of a formulation of spores degrading PLA, from 35 to 55% by weight of PLA and from 20 to 40% by weight of wheat flour, more preferably about 25% by weight of a formulation of spores degrading PLA, about 45% by weight of PLA and about 30% by weight of wheat flour.

In a particular embodiment, the masterbatch composition comprises from 20 to 60% by weight of a formulation of lipase, from 30 to 70% by weight of PCL and from 1 to 30% by weight of $CaCO_3$, preferably from 30 to 50% by weight of a formulation of lipase, from 40 to 60% by weight of PCL and from 1 to 20% by weight of $CaCO_3$, more preferably about 40% by weight of a formulation of lipase, about 50% by weight of PCL and about 10% by weight of $CaCO_3$.

In another particular embodiment, the masterbatch composition comprises from 15 to 50% by weight of a formulation of a PLA-degrading protease and from 50 to 85% by weight of PBAT, preferably from 20 to 40% by weight of a formulation of a PLA-degrading protease and from 60 to 80% by weight of PBAT, more preferably about 40% by weight of a formulation of a PLA-degrading protease and about 60% by weight of PBAT.

In another particular embodiment, the masterbatch composition comprises from 15 to 50% by weight of a formulation of a PLA-degrading protease and from 50 to 85% by weight of PCL, preferably from 20 to 40% by weight of a formulation of a PLA-degrading protease and from 60 to 80% by weight of PCL, more preferably about 40% by weight of a formulation of a PLA-degrading protease and about 60% by weight of PCL.

In a particular embodiment, the masterbatch composition comprises from 15 to 50% by weight of a formulation of PLA-degrading protease, from 40 to 80% by weight of PCL and from 1 to 30% by weight of $CaCO_3$, preferably from 20 to 40% by weight of a formulation of PLA-degrading protease, from 40 to 60% by weight of PCL and from 1 to 20% by weight of $CaCO_3$, more preferably about 30% by weight of a formulation of PLA-degrading protease, about 60% by weight of PCL and about 10% by weight of $CaCO_3$.

In a particular embodiment, the masterbatch composition comprises from 15 to 50% by weight of a formulation of oxidase, from 45 to 85% by weight of PE and from 1 to 20% by weight of pro-oxidants, preferably from 20 to 40% by weight of a formulation of oxidase, from 55 to 75% by weight of PE and from 1 to 10% by weight of pro-oxidants, more preferably about 30% by weight of a formulation of oxidase, about 65% by weight of PE and about 5% by weight of pro-oxidants.

In a particular embodiment, the masterbatch composition is a biodegradable masterbatch composition complying with at least one of the relevant standards and/or labels known by a person skilled in the art such as standard EN 13432, standard ASTM D6400, OK Biodegradation Soil (Label Vinçotte), OK Biodegradation Water (Label Vinçotte), OK Compost (Label Vinçotte), OK Compost Home (Label Vinçotte).

A biodegradable masterbatch composition refers to a masterbatch composition that is at least partially transformed under environmental conditions into oligomers and/or monomers of at least one polymer of the masterbatch, water, carbon dioxide or methane and biomass. As illustrated in the examples, preferred masterbatch compositions of the invention are biodegradable in water. Preferably, about 90% by weight of the masterbatch composition is biodegraded in water within less than 90 days, more preferably within less than 60 days, even more preferably within less than 30 days. Alternatively or in addition, the masterbatch composition may be biodegraded when exposed to wet and temperature conditions that occur in landscape. Preferably, about 90% by weight of the masterbatch composition is biodegraded with less than 3 years in the environment, more preferably within less than 2 years, even more preferably within less than 1 year. Alternatively, the masterbatch composition may be biodegraded under industrial composting conditions, wherein the temperature is maintained above 50° C.

Masterbatch Production Process

The present invention also relates to a process for preparing a masterbatch composition as described above, comprising a step (a) of mixing 11% to 90% by weight based on the total weight of the masterbatch of biological entities having a polymer-degrading activity, with 10% to 89% by weight of a carrier material, and, optionally, a step (b) of conditioning said mixture of step (a) in an solid form. In a particular embodiment, the process further comprises a step of mixing at least one additive and/or at least one pro-oxidant with the biological entities and carrier material.

In a particular embodiment, the step (a) of mixing is performed at ambient temperature, i.e., a temperature below 45° C., preferably below 35° C., more preferably between 30° C. and 20° C., by mixing powders and/or liquids.

For instance, the step (a) of mixing is performed with powders of carrier material and biological entities. To this aim, the carrier and/or the biological entities can be mechanically pre-treated before the step (a) of mixing, to lead to such powder forms. Particularly, the carrier material may be crushed, and/or the biological entities may be dried or dehydrated. Preferably, the process further comprises a step of homogenisation of the powders (i.e., carrier material and biological entities), for instance by shaking or the like. Such powder mixture may be blended into an extruder, such as single-screw extruders, multi-screw extruders of either co-rotating or counter-rotating design, dispersive kneaders, reciprocating single-screw extruder (co-kneaders). Such extrusion step ensures uniformity and homogeneity of the dispersion of biological entities in the carrier material at a temperature wherein the carrier material is in a partially or totally molten state.

Alternatively, the step (a) of mixing is performed with liquid forms of carrier material and biological entities. For instance, the carrier material is diluted in a liquid before the step (a) of mixing and/or a liquid formulation of biological entities comprising a stabilizing and/or solubilizing component is used.

Alternatively, in a preferred embodiment, the step (a) of mixing is performed at a temperature at which the carrier material is in a partially or totally molten state. The step (a) of mixing may thus be performed at a temperature at or above 40° C., particularly at or above 45° C., 55° C., 60° C., 70° C., 80° C., 90° C., 100° C., or even above 150° C., depending on the nature of the carrier material and more particularly on the nature of the polymer. Typically, this temperature does not exceed 300° C. More particularly, the temperature does not exceed 250° C. The temperature of the mixing step can be adapted by a person skilled in the art depending on the type of carrier, polymer and/or filler used for the production of the masterbatch composition. Particularly, the temperature is chosen according to the melting point, or melting temperature of the components of the carrier material. In a particular embodiment, the step (a) of mixing is performed at the melting point of the polymer of the carrier material. The polymer is then in a partially or totally molten state. In another embodiment, the step (a) of mixing is performed at a temperature between the glass transition temperature (Tg) and the melting point of said polymer. In another particular embodiment, the step (a) of mixing is performed at a temperature above the melting point of said polymer.

In a particular embodiment, the masterbatch composition may be produced by a process called "compounding", usually an extrusion-granulation process, in which the carrier material is melted and mixed with biological entities. Compounding combines mixing and blending techniques during a heat process, in order to ensure uniformity, homogeneity and dispersion in the final compound. The compounding is a technique known by a person skilled in the art. Such compounding process may be carried out with an extruder, such as single-screw extruders, multi-screw extruders of either co-rotating or counter-rotating design, dispersive kneaders, reciprocating single-screw extruder (co-kneaders).

In another particular embodiment, the masterbatch composition may be produced by a process, called "pastillation", as disclosed in patent EP 2 173 529.

More generally, the step (a) of mixing may be carried out with an extruder, wherein the carrier material is heated and melted and mixed with the biological entities.

In a preferred embodiment, the extruder used for the production of the masterbatch composition is a multi-screw extruder, preferably a twin-screw extruder, more preferably a co-rotative twin-screw extruder. In a particular embodiment, the extruder further comprises, after the screws, a static mixer. In another embodiment, the extruder is used with a die pierced with holes, preferably a two holes die.

In a preferred embodiment, the residence time of the mixture in the extruder is comprised between 5 seconds and 3 minutes, preferably is less than 2 minutes, more preferably less than 1 minute. When the masterbatch comprises a polymer with a melting temperature below 180° C., the residence time of the mixture in the extruder is preferably less than 2 minutes.

One skilled in the art will easily adapt the characteristics of the extruder (e.g., the length and diameter of the strew(s), etc.), and the residence time to the carrier material, the additives, and the type of masterbatch composition intended.

The carrier material may be introduced in the extruder in a powder or granulated form, preferably in a granulated form.

As disclosed above, the biological entities may be introduced in the extruder in a powder or liquid form such as a liquid formulation comprising a stabilizing and/or solubilizing component (e.g., water, glycerol, sorbitol, dextrin, including maltodextrine and cyclodextrine, starch, glycol such as propanediol, salt, etc.).

Advantageously, the biological entities are introduced at a late stage of the mixing step, and more particularly once the carrier material is in a partially or totally molten state. Thus, the exposure to elevated temperature is reduced. Preferably, the residence time of the biological entities in the extruder is half as long as the residence time of the carrier material, or less.

According to the invention, after the step (a) of mixing, the mixture may be conditioned (b) in any suitable solid form. In this regard, in a preferred embodiment, the liquid or melted mixture is shaped into a rod through a die. The rod is then cooled, and optionally dried before to be chopped in the form of granulates and/or pastilles of masterbatch. In a further embodiment, said granulates of masterbatch may be pulverized or micronized to produce a powder of said masterbatch.

When the mixture issued of step (a) is a powder mixture, it is possible to submit the powder mixture to an extrusion-granulation process, preferably in an extruder so that the mixture is in a partially or totally molten state, before step (b).

Alternatively, the mixture of biological entities and carrier material powders issued of step (a) is agglomerated in a solid physical form.

Alternatively, the masterbatch composition may be produced by processes of enzyme adsorption, such as the ones described in: Jesionowski et al., Adsorption (2014) 20:801-821. Such processes are well known by a person skilled in the art and will be easily adapted depending on the type of masterbatch composition, of biological entities and/or of the carrier material that will incorporate the masterbatch.

Particularly, the masterbatch composition may be produced by any techniques known by a person skilled in the art depending on the type of masterbatch composition.

Process of Manufacturing Plastic Articles

The invention also relates to the use of the masterbatch composition of the invention for manufacturing plastic articles with improved degradability or control of degradability. The masterbatch composition of the invention may be easily used to supply biological entities that have a polymer-degrading activity to a polymer during the manufacturing process. According to the invention, the biological entities are selected among the biological entities able to degrade the polymer of the plastic articles. Surprisingly, the inventors have discovered that the biological entities still exhibit a polymer-degrading activity, even after the heat treatment during which the masterbatch composition is mixed with the molten polymer and the mixture shaped into the intended form. Different amounts of the masterbatch composition may be added to the polymer, depending on the nature of the biological entities, of the polymer, on the type of plastic articles and their uses, etc. Furthermore, the resulting plastic articles show a good dispersion and distribution rate of said biological entities.

It is also an object of the invention to provide a plastic article made from the masterbatch composition of the invention, wherein the biological entities of the masterbatch composition are suitable for degrading at least one polymer of the plastic article.

The invention relates to a method for manufacturing a plastic article comprising at least one polymer, the method comprising:

A. providing a masterbatch composition of the invention, wherein the biological entities are suitable for degrading said at least one polymer of the plastic article, and B. introducing said masterbatch composition in said at least one polymer.

Advantageously, the polymer is selected from natural or synthetic polymers, and/or derivatives and/or mixtures thereof. Natural polymers are preferably selected, without limitation, from the group consisting of lignin, or polysaccharides such as cellulose or hemi-cellulose, starch, chitin, chitosan and derivatives thereof and blends/mixtures of these materials. In a particular embodiment, the natural polymer is plasticized before incorporation. Synthetic polymers are preferably selected, without limitation, from the group consisting of polyolefins, aliphatic or semi-aromatic polyesters, polyamides, polyurethanes, or vinyl polymers and derivatives thereof and mixtures thereof.

The carrier material of the masterbatch composition is advantageously compatible with the polymer that will incorporate said masterbatch. In a particular embodiment, the polymer of the plastic article is the same as the polymer of the masterbatch composition.

In another embodiment, the polymer of the plastic article is different from the polymer of the masterbatch composition, and the masterbatch composition comprises a polymer and biological entities that are not suitable for degrading the polymer of the masterbatch composition. In this particular embodiment, the carrier material of the masterbatch comprises at least one polymer that has a fusion temperature below 180° C., or below 150° C., and/or a glass transition temperature below 70° C., preferably selected from the group consisting of PLA, PCL, PBAT, PHA, PBS and EVA. Preferably, the carrier material of the masterbatch comprises at least one polymer that has a melting temperature below 120° C., or below 100° C., and/or a glass transition temperature below 30° C., preferably selected from the group consisting of PCL, PBAT, and EVA.

Alternatively, the masterbatch composition comprises a "universal" polymer, i.e., a polymer that is compatible with a broad range of polymers. Generally known universal masterbatch compositions utilize ethylene vinyl acetate copolymer (EVA) as a carrier material. Accordingly, the masterbatch composition cannot be degraded by the biological entities contained therein. Advantageously, step B is implemented at a temperature at which the polymer that will incorporate the masterbatch is in a partially or totally molten state. For instance, step B may be performed at a temperature above 55° C., particularly above 60° C., 70° C., 80° C., 90° C., 100° C., or even above 150° C., depending on the nature of the polymer that will incorporate the masterbatch composition. Typically, this temperature does not exceed 300° C. More particularly, the temperature does not exceed 250° C. The temperature of the mixing step can be adapted by a person skilled in the art depending on the type of the masterbatch composition, the polymer that will incorporate the masterbatch and/or the kind of plastic articles intended. Particularly, the temperature is chosen according to the melting point, or melting temperature, of the polymer that will incorporate the masterbatch.

In a particular embodiment, step B is performed at the melting point of said polymer. The polymer is then in a partially or totally molten state. In another embodiment, step B is performed at a temperature above the glass transition temperature (Tg) and/or between the glass transition temperature (Tg) and the melting point of said polymer. In another particular embodiment, step B is performed at a temperature above the melting point of said polymer.

Typically, said step B may be carried out by extrusion, extrusion-compounding, extrusion blow-molding, cast film extrusion, calendering and thermoforming, injection-molding, compression molding, extrusion-swelling, rotary molding, ironing, coating, stratification, expansion, pultrusion, compression-granulation, or 3D printing. Such operations are well known by the person skilled in the art, who will easily adapt the process conditions (e.g., temperature, residence time, etc.).

In a particular embodiment, step B is implemented with a solid masterbatch composition such as powder or granulates. Particularly, the polymer is introduced in step B under a powder or granulated form, preferably under a granulated form. In another embodiment, step B is implemented with a liquid masterbatch composition.

In a particular embodiment, the polymer and the masterbatch composition are introduced separately in a device used to perform step B. Advantageously, the polymer is introduced first, and the masterbatch composition secondly. Preferably, the polymer is already in a partially or totally molten state when the masterbatch composition is introduced in said device.

In another particular embodiment, the polymer and the masterbatch composition are introduced simultaneously in the device used to perform step B. To this aim, the masterbatch composition and the polymer may be advantageously mixed together by shaking or the like, preferably at ambient temperature, before step B. Advantageously, this embodiment is performed using solid forms of masterbatch composition and polymer.

In a particular embodiment, 0.01 to 20% by weight of masterbatch composition are added to the polymer, compared to the final weight of the plastic article, preferably less than 15%, more preferably less than 10%, and even more preferable less than 5%. In another particular embodiment, between 25 and 40% by weight of masterbatch composition are added to the polymer, compared to the final weight of the plastic article, preferably up to 30%, more preferably up to 40%.

In a particular embodiment, 1% to 5% by weight of masterbatch composition is incorporated and/or mixed to 95% to 99% by weight of a polymer in a partially or totally molten state.

Advantageously, the plastic article is a biodegradable plastic article complying with at least one of the relevant standards and/or labels known by a person skilled in the art such as standard EN 13432, standard ASTM D6400, OK Biodegradation Soil (Label Vinçotte), OK Biodegradation Water (Label Vinçotte), OK Compost (Label Vinçotte), OK Compost Home (Label Vinçotte).

A biodegradable plastic article refers to a plastic that is at least partially transformed under environmental conditions into oligomers and/or monomers of at least one polymer of the masterbatch, water, carbon dioxide or methane and biomass. For instance, the plastic article is biodegradable in water. Preferably, about 90% by weight of the plastic article is biodegraded in water within less than 90 days, more preferably within less than 60 days, even more preferably within less than 30 days. More preferably, the plastic article may be biodegraded when exposed to wet and temperature conditions that occur in landscape. Preferably, about 90% by weight of the plastic article is biodegraded with less than 3 years in the environment, more preferably within less than 2 years, even more preferably within less than 1 year. Alternatively, the plastic article may be biodegraded under industrial composting conditions, wherein the temperature is maintained above 50° C.

The invention also provides a method for increasing the biodegradability of a plastic article comprising at least one polymer, wherein said polymer is mixed with a masterbatch composition of the invention that comprises biological entities able to degrade said polymer, and a plastic article is further manufactured with said mixture.

The use of the masterbatch composition of the invention, wherein the biological entities are present in great amount, preserves their polymer-degrading activity, even after multiple heat treatments. Accordingly, the plastic articles obtained from mixing a polymer with a masterbatch composition comprising a high concentration of active biological entities exhibit a better biodegradability compared to plastic articles deprived of such biological entities. Interestingly, said plastic articles also exhibit a better biodegradability compared to plastic articles wherein biological entities have been incorporated directly to the polymer of the plastic article.

EXAMPLES

Example 1—Preparation of a Masterbatch Composition Comprising PCL and Lipase Under Granulated Form A masterbatch composition has been prepared comprising PCL in granulated form (polycaprolactone polymer, CAPA 6500 by Perstorp) and a Lipase PS enzyme under solid form (Amano Lipase PS by Sigma Aldrich).

A compounding machine, or co-rotating twin-screw extruder, has been used ("Coperion ZSK 18 megalab"). This compounding machine comprised successively a first feed element, two mixing elements, and a second feed element (see FIG. 1A). The compounding machine comprised nine successive heating zones Z1 to Z9 (see FIG. 1B), wherein the temperature may be independently controlled and regulated. An additional zone Z10 was present after zone Z9, corresponding to the head of the twin-screw.

According to this experiment, 50% by weight of the polycaprolactone have been mixed with 50% by weight of the lipase, and extruded, with the temperature profile described in table 1 below.

TABLE 1

| temperature profile of the compounding machine | | | | | | | | | |
|---|---|---|---|---|---|---|---|---|---|
| Zone | | | | | | | | | |
| Z1 | Z2 | Z3 | Z4 | Z5 | Z6 | Z7 | Z8 | Z9 | Z10 (head) |
| T° C. 50° C. | 80° C. | 80° C. | 80° C. | 60° C. | 60° C. | 60° C. | 60° C. | 60° C. | 60° C. |

The polymer was introduced in the principal hopper (before Z1 zone) with a flow (weight scale) of 2 kg/h. The polymer went through zones Z1 to Z5 where the temperature was increased up to 80° C. (Z4) leading to molten polymer. The biological entities (i.e., the lipase formulation) were introduced with a flow of 2 kg/h, in zone Z6, through side feeder No 2, wherein the temperature has decreased up to 60° C.

Biological entities and polymer were then mixed together from zones Z7 to zone Z9, through the rotation of the twin-screw at 300 Rpm. The residence time from Z1 to Z9 was approximately 1 minute. The mix of polymer and biological entities then arrived in the screw head (Z10), comprising two holes of 2.5 mm diameter, wherein the mix was pushed in order to form granular shapes called pellets, which are then cooled in water and dried before conditioning. The temperature at the end of the screw was measured to be 69° C.

A masterbatch composition under granulated form was obtained, that contained 50% by weight of polymer and 50% by weight of biological entities based on the total weight of the masterbatch composition.

Example 2—Preparation of a Masterbatch Composition Comprising PLA and PLA Depolymerase Under Granulated Form A masterbatch composition is prepared, comprising PLA polymer (polylactic acid PLE 003 from Natureplast) in granulated form, that is previously dried at 65° C. for 4 hours, and a liquid formulation of PLA depolymerase enzyme (70% of proteinase K from Sigma Aldrich under powder form resuspended in 30% of glycerol), using the compounding machine as described in example 1.

According to this experiment, 70% by weight of PLA is mixed with 30% by weight of liquid formulation of PLA depolymerase, and extruded, with the temperature profile described in table 2 below.

The PLA is introduced in the principal hopper (before Z1 zone) with a flow of 7 kg/h. The PLA goes through zones Z1 to Z5, wherein the temperature was increased up to 180° C. (Z4) leading to molten PLA. The enzymes are then introduced with a flow of 3 kg/h, in Z6, through the side feeder No 2, where the temperature is decreased to 140° C.

Enzyme and PLA are then mixed together from zones Z7 to zone Z9, through the rotation of the twin-screw at 200 Rpm. The residence time from Z1 to Z9 is approximately 1 minute and 30 seconds. The mix of PLA and biological entities then arrive in the screw head (Z10) comprising two holes of a diameter of 2.5 mm, wherein the mix is pushed in order to form pellets, which are then cooled in water and dried before conditioning. A masterbatch composition under granulated form is obtained, that contains 70% by weight of PLA, and 30% by weight of the formulation of PLA depolymerase.

Example 3—Preparation of a Masterbatch Composition Comprising PLA, Wheat Flour and Bacterial Spores Under Granulated Form A masterbatch composition is prepared using the compounding machine as described in example 1. The masterbatch comprises:

PLA polymer (polylactic acid PLE 003 from Natureplast) in granulated form, that has been previously dried at 65° C. for 4 hours, wheat flour also previously dried, and A spore preparation, obtained by the lyophilization of a culture supernatant of *Bacillus licheniformis*.

According to this experiment, 45% by weight of PLA are mixed with 30% by weight of wheat flour and 25% by weight of the spore preparation, and then extruded, with the temperature profile described in table 3 below.

TABLE 2

| temperature profile of the compounding machine | | | | | | | | | |
|---|---|---|---|---|---|---|---|---|---|
| Zone | | | | | | | | | |
| Z1 | Z2 | Z3 | Z4 | Z5 | Z6 | Z7 | Z8 | Z9 | Z10 (head) |
| T° C. 135° C. | 150° C. | 170° C. | 180° C. | 140° C. | 140° C. | 140° C. | 140° C. | 140° C. | 140° C. |

TABLE 3 temperature profile of the compounding machine

| | | | | Zone | | | | | |
|---|---|---|---|---|---|---|---|---|---|
| Z1 | Z2 | Z3 | Z4 | Z5 | Z6 | Z7 | Z8 | Z9 | Z10 (head) |
| T° C. 135° C. | 150° C. | 170° C. | 180° C. | 140° C. | 140° C. | 140° C. | 140° C. | 140° C. | 140° C. |

The PLA is introduced in the principal hopper (before Z1 zone) with a flow of 4.5 kg/h. The wheat flour is introduced in the side feeder No 1 (Z3) with a flow of 3 kg/h where the PLA is already in a partially or total molten state. The mix goes through zones Z3 to Z5, wherein the temperature is increased up to 180° C. (Z4) leading to a molten mix of PLA and wheat flour. The spores are then introduced with a flow of 2.5 kg/h, in Z6, through the side feeder No 2, where the temperature is decreased to 140° C.

Spores, PLA and flour are then mixed together from zones Z7 to zone Z9, through the rotation of the twin-screw at 200 Rpm. The residence time from Z1 to Z9 is approximately 1 minute and 30 seconds. The mix of PLA, flour and spores then arrive in the screw head (Z10) comprising two holes of a diameter of 2.5 mm, wherein the mix is pushed in order to form pellets, which are then cooled in water and dried before conditioning. A masterbatch composition under granulated form is obtained, that contains 45% by weight of PLA mixed with 30% by weight of wheat flour and 25% by weight of the spore preparation.

Example 4—Preparation of a Masterbatch Composition Comprising PCL, Calcium Carbonate and Lipase Under Granulated Form A masterbatch composition is prepared using the compounding machine as described in example 1. The masterbatch comprises:
  PCL in granulated form (polycaprolactone polymer, CAPA 6500 by Perstorp),
  A filler calcium carbonate ($CaCO_3$),
  Lipase PS enzymes under solid form (Amano Lipase PS by Sigma Aldrich).

According to this experiment, 50% by weight of PCL are mixed with 10% by weight of $CaCO_3$ and 40% by weight of enzymes, and extruded, with the temperature profile described in table 4 below.

The PCL is introduced in the principal hopper (before Z1 zone) with a flow of 5 kg/h. The $CaCO_3$ is introduced in the Side feeder No 1 (Z3) with a flow of 1 kg/h where the PCL is already in a partially or total molten state. The mix goes through zones Z3 to Z5, wherein the temperature is increased up to 80° C. (Z4) leading to a molten mix of polymer PCL and filler $CaCO_3$. The enzymes are then introduced with a flow of 4 kg/h, in Z6, through the side feeder No 2, where the temperature is decreased to 60° C.

Enzymes, PCL and $CaCO_3$ are then mixed together from zones Z7 to zone Z9, through the rotation of the twin-screw at 200 Rpm. The residence time from Z1 to Z9 is approximately 1 minute and 30 seconds. The mix of PCL, $CaCO_3$ and enzymes then arrive in the screw head (Z10) comprising two holes of a diameter of 2.5 mm, wherein the mix is pushed in order to form pellets, which are then cooled in water and dried before conditioning. A masterbatch composition under granulated form is obtained, that contains 50% by weight of PCL mixed with 10% by weight of $CaCO_3$ and 40% by weight of enzymes.

Example 5—Preparation of a Masterbatch Composition Comprising PE, Laccases and Pro-Oxidants Under Granulated Form A masterbatch composition is prepared using the compounding machine as described in example 1. The masterbatch comprises:
  Polyethylene (PE) in granulated form (Green PE from Braskem),
  A laccase formulation produced from *Rhodococcus* sp. (e.g.; *Rhodococcus ruber* DSM 45332 and/or *R. rhodochrous* ATCC 29672),
  Pro-oxidants Fe—Mn.

According to this experiment, 65% by weight of PE are mixed with 5% by weight of pro-oxidants and 30% by weight of laccase formulation, and extruded, with the temperature profile described in table 5 below.

TABLE 4 temperature profile of the compounding machine

| | | | | Zone | | | | | |
|---|---|---|---|---|---|---|---|---|---|
| Z1 | Z2 | Z3 | Z4 | Z5 | Z6 | Z7 | Z8 | Z9 | Z10 (head) |
| T° C. 50° C. | 80° C. | 80° C. | 80° C. | 60° C. | 60° C. | 60° C. | 60° C. | 60° C. | 60° C. |

TABLE 5

Temperature profile of the compounding machine

| | | | | Zone | | | | | |
|---|---|---|---|---|---|---|---|---|---|
| Z1 | Z2 | Z3 | Z4 | Z5 | Z6 | Z7 | Z8 | Z9 | Z10 (head) |
| T° C. 130° C. | 135° C. | 135° C. | 145° C. | 140° C. | 140° C. | 150° C. | 160° C. | 180° C. | 190° C. |

The PE is introduced in the principal hopper (before Z1 zone) with a flow of 6.5 kg/h. The pro-oxidants are introduced in the Side feeder No 1 (Z3) with a flow of 0.5 kg/h. The mix goes through zones Z3 to Z5, wherein the temperature is increased up to 145° C. (Z4) leading to a molten mix of PE and pro-oxidants. The enzymes are then introduced with a flow of 3 kg/h, in Z6, through the side feeder No 2, where the temperature is decreased to 140° C.

Enzymes, PE and pro-oxidants are then mixed together from zones Z7 to zone Z9, through the rotation of the twin-screw at 200 Rpm. The residence time from Z1 to Z9 is approximately 1 minute and 30 seconds. The mix of PE, pro-oxidants and enzymes then arrive in the screw head (Z10) comprising two holes of a diameter of 2.5 mm, wherein the mix is pushed in order to form pellets, which are then cooled in water and dried before conditioning. A masterbatch composition under granulated form is obtained, that contain 65% by weight of PE mixed with 5% by weight of pro-oxidants and 30% by weight of enzymes.

Example 6—Preparation of a Masterbatch Composition Comprising PCL and Lipase Under Powder Form A masterbatch composition has been prepared comprising PCL in granulated form (polycaprolactone polymer, CAPA 6500 by Perstorp), further micronized to produce a powder of said polymer, and a Lipase PS enzyme under a powder form (Amano Lipase PS by Sigma Aldrich).

100 grams of PCL and 100 grams of Lipase PS enzyme are mixed by shaking at ambient temperature, about 25° C.

A masterbatch composition under powder form is thus obtained, that contained 50% by weight of PCL mixed with 50% by weight of biological entities.

Example 7—Use of a Masterbatch Composition for Manufacturing Biodegradable Plastic Articles The granulated masterbatch composition of Example 1 was used to produce biodegradable polycaprolactone-based plastic articles through an extrusion-compounding process and a biodegradable polycaprolactone-based film through a cast film extrusion process. The biodegradability of said plastic articles and films has been further tested.

7A—Process of Manufacturing Plastic Articles Using a Masterbatch Composition of the Invention Through an Extrusion-Compounding Process The plastic articles were produced using the compounding machine of Example 1. The temperature profile of the different zones was adapted to the polymer that incorporated the masterbatch and the kind of articles (see table 6 below). More particularly, two different temperature profiles were tested for their impact on the biological entities activity.

The polymer of the plastic articles was polycaprolactone (PCL CAPA 6500 by Perstorp), and the masterbatch composition was the one obtained according to example 1.

TABLE 6

Temperature profiles in the compounding machine

| | | | | | Zone | | | | | |
|---|---|---|---|---|---|---|---|---|---|---|
| | Z1 | Z2 | Z3 | Z4 | Z5 | Z6 | Z7 | Z8 | Z9 | Z10 head |
| Profile 1 | 55° C. | 80° C. | 100° C. | 120° C. | 140° C. | 140° C. | 140° C. | 140° C. | 140° C. | 140° C. |
| Profile 2 | 135° C. | 150° C. | 170° C. | 180° C. | 140° C. | 140° C. | 140° C. | 140° C. | 140° C. | 140° C. |

PCL was introduced in granulated form in the hopper (before Z1) at a weight scale of 7.68 kg/h. The polymer went through zones Z1 to Z5 in order to be melted. In the temperature profile 2, the polymer went through higher temperatures. The masterbatch composition under granulated form was then introduced in the side feeder No 2 (Z6), at a weight scale of 0.32 kg/h. 4% by weight of masterbatch composition based on the total weight of the mixture was thus incorporated. Masterbatch composition and polymer were mixed together from zones Z7 to zone Z9, with the rotation of the twin-screw at 200 Rpm.

The mixture of melted polymer and masterbatch composition then arrived at an output flow rate of 8 kg/h in the screw head (Z10), comprising two holes of a diameter of 2.5 mm, wherein the mixture was pushed in order to form plastic pellets.

The plastic articles obtained thus contain 2% by weight of biological entities and 98% by weight of PCL.

7B—Tests of Biodegradability of Plastics Articles Made from 7A

Different tests of biodegradability have been performed, using:
  two plastic articles of example 7A, obtained with the two different temperature profiles;
  the masterbatch composition of Example 1;
  a commercial polycaprolactone (PCL CAPA 6500 by Perstorp).

The tests of biodegradability were performed in water. Empty tea bags have been used to protect the samples during the biodegradation test. The degradability of the different products was measured by means of the loss of mass, after one week, two weeks, four weeks and eight weeks.

First, the products and empty tea bags have been dried for one night at 40° C. in a ventilated oven. Then, they have been maintained for 1 hour in a chamber thermally regulated at 23° C. and 50% humidity. After that, several samples of about 5 g of each product were placed in different tea bags (accurately measured, to the nearest milligram). The tea bags were then immersed in a tank of 1 Liter water (Cristalline®). A sample of each product was then withdrawn after one week, two weeks, four weeks or eight weeks and maintained for one night in a ventilated oven at 40° C. Then, the samples were maintained for 1 hour in a chamber thermally regulated at 23° C. and 50% humidity. The masses of the samples were then accurately measured, to the nearest milligram, to evaluate the loss of mass.

The results obtained show a biodegradability of 90% after eight weeks of incubation in water, for the plastic articles of example 7A, whereas the commercial CAPA polymer did not exhibit any loss of weight after eight weeks (see FIG. 2). The masterbatch composition of Example 1 presents a loss of mass of more than 90% after two weeks.

These experiments demonstrate that the biological entities withstood the successive heat treatments inflicted during the process for preparing the masterbatch and the process of manufacturing the plastic articles.

7C—Process of Manufacturing a Plastic Film Using a Masterbatch of the Invention Through a Cast Film Extrusion Process The granulated masterbatch of Example 1 has been mixed with polycaprolactone (PCL CAPA 6500 made by Perstorp) using a single-screw extruder and a cast film extrusion process.

Extruder: "Monovis Rheocord Sustem 40 (A Haake Buchler Product)". The extruder comprised three zones from Z1 to Z3, and an extrusion die, wherein the temperature may be independently controlled and regulated. The extruder is approximately 40 centimeters long. A roller calendar system from ThermoElectron Corporation was fixed to the end of the extruder to produce a film with a thickness of 100 µm and a width of 5 cm.

In this example, the masterbatch of the invention was incorporated at a ratio of 4% based on the total weight of the final product.

The masterbatch of Example 1 (20 grams) and the polymer CAPA 6500 (480 grams), both under granulated form, were first shaken together. Granulates were then dried one night under vacuum at 30° C., and introduced in the extruder before Z1. The granulates were melted and mixed from Z1 to Z3 until the extrusion die thanks to the single screw rotating between 18-20 Rpm. The residence time of the mix was about 30 seconds. In this particular example, the temperatures of Z1, Z2, Z3 and the extrusion die were all regulated at 140° C.

The plastic film produced contained 2% by weight of biological entities and 98% per weight of polymer.

7D—Test of Biodegradability of Plastic Film from 7C

Different tests of biodegradability have been performed, using:
The original polymer polycaprolactone (PCL CAPA 6500 made by Perstorp),
The plastic film of 7C.

The tests of biodegradability were performed in water. Winter crop protection veils have been used to protect the samples during the biodegradation test. The degradability of the different products was measured by means of the loss of mass, after one week, two weeks, four weeks and eight weeks.

First, the products and winter crop protection veils have been dried for one night at 40° C. in a ventilated oven. Then, they have been maintained for 1 hour in a chamber thermally regulated at 23° C. and 50% humidity. After that, several samples of each product were placed in different winter crop protection veils. The veils were then immersed in a tank of 1 Liter water (Cristalline®). A sample of each product was then withdrawn after one week, two weeks, four weeks or eight weeks and maintained for one night in a ventilated oven at 40° C. Then, the samples were maintained for 1 hour in a chamber thermally regulated at 23° C. and 50% humidity. The masses of the samples were then accurately measured, to the nearest milligram, to evaluate the loss of mass.

The results showed a biodegradability of the plastic film over 10% after eight weeks of incubation in water, whereas the commercial CAPA polymer did not exhibit any loss of weight after eight weeks (see FIG. 3).

These experiments demonstrate that the biological entities withstood the successive heat treatments inflicted during the process for preparing the masterbatch and the process of manufacturing the plastic articles.

Example 8—Masterbatch Composition with Polylactic Acid (PLA) and Protease and Plastic Article 8A. Process of Manufacturing Masterbatch A masterbatch composition has been prepared comprising polylactic acid in powder form (polylactic acid, PLA 4043D from NatureWorks), and protease enzyme (Savinase® 16L by Novozymes) formulated under solid form.

PLA was obtained from granulates immersed in liquid nitrogen and micronized using an Ultra Centrifugal Mill ZM 200 system to a fine powder <500 µm size.

Solid Form of Savinase® 16L was obtained from commercial liquid form by ultrafiltration on 3.5 kDa membrane, diafiltration, addition of dextrin and drying by freeze-drying. Savinase® 16L is known as degrading PLA (Degradation of Polylactide by commercial proteases; Y. Oda, A. Yonetsu, T. Urakami and K. Tonomura; 2000).

A compounding machine, or co-rotating twin-screw extruder, has been used for the production of the masterbatch compositions ("Haake MiniLab II ThermoFisher"). This compounding machine comprised successively a manual feed element, two co-rotating screw and the head of the twin screw.

According to this experiment, two masterbatch compositions (Table 7) were made:

TABLE 7

| Masterbatch compositions | | |
|---|---|---|
| | PLA | Protease |
| MB1 | 80% | 20% |
| MB2 | 60% | 40% |

Percentage was calculated based on the total weight of the masterbatch composition.

Protease (Biological entities) and polymer were mixed together by manual shaking before introduction in the compounding machine. The mix was then introduced in the feeding zone, and push into the screw extruder applying manual pressure. The mix went through co-rotating screws, using a rotation speed of 80 RPM. The temperature was fixed to 150° C. The mix of polymer, biological entities then arrived in the screw head, comprising one hole of 0.4 mm in diameter, wherein the mix was pushed in order to form strip shapes. This extrudate was then cut with cutting pliers to obtain granulate form.

Masterbatch composition under granulated form were obtained, that contained from 60 to 80% by weight of polymer, and from 20 to 40% by weight of biological entities.

8B—Tests of Biodegradability of the Masterbatch Compositions

Tests of biodegradability of masterbatches MB1 and MB2 have been performed.

100 mg of each sample were weighted and introduced in dialysis tubing. 3 mL of 0.1 M Tris-HCl buffer pH 9.5 were added in the dialysis tubing before closing it. The dialysis tubing was then introduced in a plastic bottle containing 50 mL of 0.1 M Tris-HCl buffer pH 9.5.

The depolymerization was started by incubating each sample at 45° C., 150 rpm in an Infors HT Multitron Pro incubation shaker. Aliquots of 1 mL of buffer were sampled regularly, filtered on 0.22 μm syringe filter, and analyzed by High Pressure Liquid Chromatography (HPLC) with an Aminex HPX-87H column to monitor the liberation of lactic acid (LA) and lactic acid dimer (DP2). Chromatography system used was an Ultimate 3000 UHPLC system (Thermo Fisher Scientific, Inc. Waltham, Mass., USA) including a pump module, an autosampler, a column oven thermostated at 50° C., and an UV detector at 220 nm. Eluent was 5 mM $H_2SO_4$. Injection was 20 μL of sample. LA was measured according to standard curves prepared from commercial LA.

Percentage of degradation is calculated by the molar ratio of LA plus the LA contained in DP2 at a given time versus the LA contained initially in the PLA. Results of depolymerization, after 6 days, are shown in FIG. 4. Interestingly, even if the degradation rate of MB1 is high, the degradation rate of MB2, containing twice the quantity of biological entities compared to MB1, is twice higher.

8C—Process of Manufacturing Plastic Articles

The granulated masterbatch compositions have been used to produce biodegradable polylactic acid-based plastic articles through an extrusion process. The biodegradability of said plastic articles has been further tested.

The plastic articles were produced using the compounding machine of Example 8A. The temperature profile was adapted to the polymer that incorporated the masterbatch.

The polymer of the plastic articles was polylactic-acid (PLA 4043D by NatureWorks, same as example 8A) and the masterbatch compositions under granulated form were the ones obtained according to example 8A. Each masterbatch composition was added at the equivalent of 20% by weight based on the total weight of the final plastic articles. Calcium carbonate under a powder form (from OMYA) was also added, equivalent to 5% by weight of the final plastic articles. PLA under a powder form was therefore added at the equivalent of 75% by weight based on the total weight of the final plastic articles.

PLA is used under a powder form (<500 μm) obtained from PLA granulate immersed in liquid nitrogen and micronized using an Ultra Centrifugal Mill ZM 200 system. Masterbatch, polymer and $CaCO_3$ were mixed together by manual shaking before introduction in the compounding machine. Extrusion was made following the protocol described in example 8A. Only the temperature of extrusion was modified, fixed at 155° C.

TABLE 8

Composition of the plastic articles

| Formulation | Final Composition | Extrusion Temperature (° C.) |
|---|---|---|
| A 75% PLA + 20% MB1 + 5% CaCO3 | 91% PLA + 4% Protease + 5% CaCO3 | 155 |
| B 75% PLA + 20% MB2 + 5% CaCO3 | 85% PLA + 8% Protease + 5% CaCO3 | 155 |

8D—Tests of Biodegradability of the Plastics Articles

Tests of biodegradability have been performed, using plastic articles A and B.

The subsequent depolymerization was performed using the same material and method as exposed in Example 8B. Percentage of degradation is calculated by the molar ratio of LA plus the LA contained in DP2 at a given time versus the LA contained initially in the PLA.

As shown in FIG. 5, after 16 days, the degradation rate of the plastic article A (containing 4% of biological entities) is about 6%, whereas, the degradation rate of the plastic article B (containing 8% of biological entities) is about 12%. Both plastic articles exhibit a degradation rate. Interestingly, the activity of the biological entities into the plastic articles is still present so as the one in the masterbatch, confirming that the activity of biological entities is maintained even after two temperature treatments.

Example 9—Masterbatch Composition with PolyButylene Adipate Terephthalate (PBAT) and Protease and Plastic Articles 9A—Process of Manufacturing Masterbatch A masterbatch composition has been prepared comprising polymer in powder form (Polybutylene adipate terephthalate, PBAT Ecoflex Blend C1200 from BASF), and protease enzyme (Savinase® 16L by Novozymes) formulated under solid form. The protease is known to have PLA-degrading activity.

PBAT powder was obtained from granulate immersed in liquid nitrogen and micronized using an Ultra Centrifugal Mill ZM 200 system to a fine powder <500 μm size. Solid Form of Savinase 16L, was obtained from commercial liquid form by ultrafiltration on 3.5 kDa membrane, diafiltration, addition of dextrin and drying by freeze-drying.

Composition of masterbatch is the following: 60% by weight of PBAT and 40% by weight of protease. Percentage are calculated based on the total weight of the masterbatch composition.

The same compounding machine and extrusion protocol have been used as in example 8A, except concerning the temperature of extrusion fixed at 120° C.

9B—Process of Manufacturing Plastic Articles

The granulated masterbatch composition of Example 9A containing a PLA-degrading protease was used to produce biodegradable PLA-based plastic article through an extrusion process. The biodegradability of said plastic article has been further tested.

The plastic article was produced using the compounding machine of Example 8A. The temperature profile was adapted to the polymer that incorporated the masterbatch.

The polymer of the plastic articles was polylactic-acid (PLA 4043D from NatureWorks, same as Example 8A) and the masterbatch composition was the one obtained according to example 9A and is used under granulated form. Masterbatch composition was added equivalent to 20% by weight based on the total weight of plastic articles formulations. Calcium carbonate under powder form (from OMYA) was also added, equivalent to 5% by weight. Thus, PLA was added at 75% by weight based on the total weight of the final plastic article. PLA was used under a powder form (<500 µm) obtained from PLA granulate immersed in liquid nitrogen and micronized using an Ultra Centrifugal Mill ZM 200 system.

Masterbatch, polymer and $CaCO_3$ were mixed together by manual shaking before introduction in the compounding machine. Extrusion was made following the protocol described in example 8A.

Composition of plastic article thus obtained is the following: 75% PLA+12% PBAT+8% Protease+5% CaC03 (by weight based on the total weight of plastic article).

9C—Tests of Biodegradability of Plastics Articles

Tests of biodegradability have been performed, using the same material and method as exposed in Example 8B. Hydrolysis of plastic articles was calculated based on LA and dimer of LA released. Percentage of degradation is calculated regarding the final percentage of PLA in the formulation.

After 4 days, the rate of depolymerization of the plastic article made from the masterbatch composition of example 9A was 48%.

Interestingly, the result of degradation of this plastic article may be compared to the one of plastic article B of example 8C, both containing 8% protease. Degradation rate of plastic article B of example 8C reach 12% after 12 days whereas plastic article of example 9C reach 48% in 4 days. This result may show that there could be an advantage to produce a masterbatch composition comprising a polymer with a lower melting temperature, i.e., needing a lower extrusion temperature, allowing a better preservation of the biological entities activity in the final plastic article.

Example 10—Masterbatch Composition with Polycaprolactone (PCL), and Protease and Plastic Articles 10A—Process of Manufacturing Masterbatch A masterbatch composition has been prepared comprising PCL in powder form (polycaprolactone polymer, CAPA 6500 from Perstorp), and a Protease enzyme Savinase® 16L by Novozymes known to have PLA-degrading activity.

PCL powder was obtained from PCL granulate immersed in liquid nitrogen and micronized using an Ultra Centrifugal Mill ZM 200 system to a fine powder <500 µm size. Solid Form of Savinase 16L was obtained from commercial liquid form by ultrafiltration on 3.5 kDa membrane, diafiltration, addition of dextrin and drying by freeze-drying.

According to this experiment, 60% by weight of the polycaprolactone have been mixed with 40% by weight of the protease (based on the total weight of masterbatch composition).

The same compounding machine and extrusion protocol have been used as in example 8A, except concerning the temperature fixed to 65° C.

10B—Process of Manufacturing Plastic Articles

The granulated masterbatch composition was used to produce biodegradable polylactic acid-based plastic articles through an extrusion process. The biodegradability of said plastic articles has been further tested.

The plastic articles were produced using the compounding machine of Example 8A. The temperature profile was adapted to the polymer that incorporated the masterbatch.

The polymer of the plastic articles was polylactic-acid (PLA 4043D from NatureWorks) and the masterbatch composition was the one obtained according to example 10A. Masterbatch under granulated form was added from 5 to 20% by weight based on the total weight of plastic articles formulations, leading to different formulations (see table 9). Calcium carbonate under powder form (from OMYA) was also added, equivalent to 5% by weight.

PLA is used under a powder form (<500 µm) obtained from PLA granulate immersed in liquid nitrogen and micronized using an Ultra Centrifugal Mill ZM 200 system.

Masterbatch, polymer and CaCo3 were mixed together by manual shaking before introduction in the compounding machine. Extrusion was made following the protocol described in example 8A. Only the temperature was modified, fixed at 150° C.

TABLE 9

Composition of plastic articles

| Formulation | Final Composition | Extrusion Temperature (° C.) |
| --- | --- | --- |
| A 75% PLA + 20% masterbatch + 5% CaC03 | 75% PLA + 12% PCL + 8% Protease 5% CaC03 | 150 |
| B 90% PLA + 5% masterbatch + 5% CaC03 | 90% PLA + 3% PCL + 2% Protease + 5% CaC03 | 150 |
| C Control sample | 75% PLA + 12% PCL + 8% Protease 5% CaC03 | 2 times at 150° c. |

A control sample (C) was made by mixing powder form of PLA (75% by weight), PCL (12% by weight), Protease (8% by weight) and CaC03 (5% by weight). Materials used were the same described in example 10A for PCL and protease and in example 9A for PLA and CaC03. Extrusion of C was made using the same compounding machine described in example 8A. The mix of powder was extruded first, according to the protocol described above. The extrudate obtained was cut with cutting pliers to obtain granulated form. This granulated form was then extruded a second time, according to the protocol described in example 8A (150° C., 80 RPM). Control sample C reflects the case when the plastic article is produced directly from a compound containing the final amount of biological entities (it has thus to be compared to formulation A).

10C—Tests of Biodegradability of Plastics Articles

Tests of biodegradability have been performed, using the same material and method as exposed in Example 8B. Percentage of degradation is calculated by the molar ratio of LA plus the LA contained in DP2 at a given time versus the LA contained initially in the PLA.

Results of depolymerization, after 8 days are shown in FIG. 6.

As expected the plastic article A exhibit a better degradation than the plastic article B, explained because the plastic article A contains four times more protease in its formulation that plastic article B.

Interestingly, the control plastic article C, which has the same final formulation as the plastic article A, shows a lower degradation rate than A. This may show that plastic articles produced from a masterbatch exhibit a better biodegradability compared to plastic articles wherein biological entities have been incorporated directly to the polymer of the plastic article.

Example 11—Masterbatch Composition with Polycaprolactone (PCL), Protease and CaC03 and Plastic Articles 11A: Process of Manufacturing Masterbatch A masterbatch composition has been prepared comprising PCL in powder form (polycaprolactone polymer, CAPA 6500 from Perstorp), a Protease enzyme (Savinase® 16L by Novozymes) formulated under solid form, known to have a PLA-degrading activity and calcium carbonate CaC03 (from OMYA).

PCL powder was obtained from PCL granulate immersed in liquid nitrogen and micronized using an Ultra Centrifugal Mill ZM 200 system to a fine powder <500 µm size. Solid Form of Savinase 16L was obtained from commercial liquid form by ultrafiltration on 3.5 kDa membrane, diafiltration, addition of dextrin and drying by lyophilisazation.

According to this experiment, 60% by weight of the polycaprolactone have been mixed with 30% by weight of the protease and 10% by weight of calcium carbonate $CaCO_3$ based on the total weight of masterbatch composition.

The same compounding machine and extrusion protocol have been used as in example 8A, except concerning the temperature fixed to 65° C.

11B—Process of Manufacturing Plastic Article

The granulated masterbatch composition was used to produce biodegradable polylactic acid-based plastic article through an extrusion process. The biodegradability of said plastic article has been further tested.

The plastic article was produced using the compounding machine of Example 8A. The temperature profile was adapted to the polymer that incorporated the masterbatch.

The polymer of the plastic articles was polylactic-acid (PLA 4043D from NatureWorks) and the masterbatch composition was the one obtained according to example 11A. Masterbatch under granulated form was added at 25% based on the total weight of plastic articles formulation.

PLA is used under a powder form (<500 µm) obtained from PLA granulate immersed in liquid nitrogen and micronized using an Ultra Centrifugal Mill ZM 200 system.

Masterbatch and polymer were mixed together by manual shaking before introduction in the compounding machine. Extrusion was made following the protocol described in example 8A. Only the temperature, was modified, fixed at 150° C.

The plastic article obtained thus contain 7.5% by weight of protease, 2.5% by weight of CaC03, 15% by weight of PCL and 75% by weight of PLA.

11C—Tests of Biodegradability of Plastics Articles

Control sample was made by mixing powder form of PLA (75% by weight), PCL (15% by weight), Protease (7.5% by weight) and CaC03 (2.5% by weight). Materials used are the same described in example 11A for PCL, protease and CaCo3, and in example 8A for PLA. Extrusion was made using the same compounding machine described in example 1A. The mix of powder was extruded a first time, according to the protocol described in example 11B. The extrudate obtained was cut with cutting pliers to obtain granulate form. This granulate form was extruded a second time, according to the protocol described in example 11B (150° C., 80 RPM). Control sample reflects then the case when the plastic article is produced directly from a compound containing the final amount of biological entities.

Tests of biodegradability have been performed, using the same material and method as exposed in Example 8B. Percentage of degradation is calculated by the molar ratio of LA plus the LA contained in DP2 at a given time versus the LA contained initially in the PLA.

Results of depolymerization, after 31 hours are shown in FIG. 7.

Interestingly, the plastic article produced from the masterbatch of Example 11A shows a better degradation rate than the control sample (8 times higher). This may show that plastic articles produced from masterbatch composition exhibit a better biodegradability compared to plastic articles wherein biological entities have been incorporated directly to the polymer of the plastic article.

The invention claimed is:

1. A masterbatch composition comprising a carrier material and biological entities having a polymer-degrading activity, wherein the carrier material comprises at least one polymer selected from cellulose, hemi-cellulose, starch, polyolefins, aliphatic or semi-aromatic polyesters, polyamides, derivatives thereof or combinations thereof and represents between 10% and 89% by weight of the composition, based on the total weight of the masterbatch composition;

the biological entities are embedded in the carrier material, wherein the biological entities represent between 11% and 90% by weight of the composition, based on the total weight of the masterbatch composition and are selected from enzymes having a polymer-degrading activity and microorganisms expressing an enzyme having a polymer-degrading activity; and the masterbatch composition is in a solid form.

2. The masterbatch composition of claim 1 wherein the carrier material further comprises a filler material, wherein the filler material is selected from the group consisting of calcium carbonate, hydrous magnesium silicate, talc, soapstone, alumnisilicate, kaolin, gypsum, glass fibers, wood flour, plant or vegetable flour, cereal flour, hemp fibers, and derivatives thereof.

3. The masterbatch composition of claim 1, wherein the carrier material further comprises a filler material, wherein the filler material is selected from the group consisting of calcium carbonate, hydrous magnesium silicate, talc, soapstone, alumnisilicate, kaolin, gypsum, glass fibers, wood flour, plant or vegetable flour, cereal flour, hemp fibers, and derivatives thereof.

4. The masterbatch composition of claim 1, wherein the carrier material further comprises a filler material, and wherein the concentration of said at least one polymer in the carrier material is higher than the concentration of the filler material.

5. The masterbatch composition of claim 1, wherein the carrier material represents between 20% and 80% by weight of the masterbatch composition.

6. The masterbatch composition of claim 1, wherein the biological entities are suitable for degrading said at least one polymer of the carrier material.

7. The masterbatch composition of claim 1, wherein the composition further comprises at least one additive, wherein the additive is selected from the group consisting of plasticizers, coloring agents, processing aids, flame retardant agents, and light stabilizers.

8. The masterbatch composition of claim 1, which comprises, based on the total weight of the masterbatch composition:
   (i) from 5 to 30% of at least one polymer,
   (ii) from 5 to 30% of at least one filler material, and
   (iii) from 30 to 70% of biological entities having a polymer-degrading activity.

9. A plastic article comprising the masterbatch composition as claimed in claim 1.

10. The masterbatch composition of claim 1, wherein said at least one polymer of the carrier material is an aliphatic polyester selected from the group consisting of polylactic acid (PLA), poly(L-lactic acid) (PLLA), poly(D-lactic acid) (PDLA), poly(D,L-lactic acid) (PDLLA), PLA stereocomplex (scPLA), polyglycolic acid (PGA), polyhydroxyalkanoate (PHA), polycaprolactone (PCL), polybutylene succinate (PBS) or at least one semi-aromatic polyesters selected from polyethylene terephthalate (PET), polytrimethylene terephthalate (PTT), polybutylene terephthalate (PBT), polyethylene isosorbide terephthalate (PEIT), polybutylene succinate adipate (PBSA), polybutylene adipate terephthalate (PBAT), polyethylene furanoate (PEF), poly(ethylene adipate) (PEA), polyethylene naphthalate (PEN), and derivatives or blends/mixtures thereof.

11. The masterbatch composition of claim 1, wherein said at least one polymer of the carrier material has a melting temperature below 180° C.

12. The masterbatch composition of claim 11, wherein the polymer is selected from the group consisting of PLA, PCL, PBAT, PHA, PBS and EVA.

13. The masterbatch composition of claim 12, wherein said at least one polymer of the carrier material is PLA and the composition comprises, based on the total weight of the masterbatch composition:
 (i) from 50 to 85% of PLA; and
 (ii) from 15 to 50% of a protease formulation as the biological entities.

14. The masterbatch composition of claim 12, wherein said at least one polymer of the carrier material is PBAT and the composition comprises, based on the total weight of the masterbatch composition:
 (i) from 50 to 85% of PBAT; and
 (ii) from 15 to 50% of a formulation of PLA-degrading protease as the biological entities.

15. The masterbatch composition of claim 12, wherein said at least one polymer of the carrier material is PCL and the composition comprises, based on the total weight of the masterbatch composition:
 (i) from 50 to 85% of PCL; and
 (ii) from 15 to 50% of a formulation of PLA-degrading protease as the biological entities.

* * * * *